United States Patent
Cahill

(10) Patent No.: US 11,609,235 B2
(45) Date of Patent: Mar. 21, 2023

(54) RAPID NATIVE SINGLE CELL MASS SPECTROMETRY

(71) Applicant: UT-Battelle, LLC, Oak Ridge, TN (US)

(72) Inventor: John F. Cahill, Knoxville, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 179 days.

(21) Appl. No.: 16/685,740

(22) Filed: Nov. 15, 2019

(65) Prior Publication Data

US 2020/0191794 A1 Jun. 18, 2020

Related U.S. Application Data

(60) Provisional application No. 62/781,048, filed on Dec. 18, 2018.

(51) Int. Cl.
*G01N 33/68* (2006.01)
*G01N 30/72* (2006.01)

(52) U.S. Cl.
CPC ..... *G01N 33/6848* (2013.01); *G01N 30/7233* (2013.01); *G01N 2560/00* (2013.01)

(58) Field of Classification Search
None
See application file for complete search history.

(56) References Cited

U.S. PATENT DOCUMENTS

| | | |
|---|---|---|
| 10,048,236 B2 | 8/2018 | Van Berkel |
| 10,060,838 B2 | 8/2018 | Kertesz et al. |
| 2011/0024615 A1 | 2/2011 | Tanner et al. |
| 2014/0070092 A1 | 3/2014 | Bandura et al. |
| 2014/0315237 A1 | 10/2014 | Masujima et al. |
| 2015/0293063 A1 | 10/2015 | Wang et al. |
| 2015/0364306 A1 | 12/2015 | Yang et al. |

(Continued)

FOREIGN PATENT DOCUMENTS

WO 2011154042 A1 12/2011

OTHER PUBLICATIONS

Cahill et al.: "Laser dissection sampling modes for direct mass spectral analysis", Rapid Communication in Mass Spectrometry 2016, 30(5), 611-619.

(Continued)

*Primary Examiner* — Xiaoyun R Xu
(74) *Attorney, Agent, or Firm* — Fox Rothschild LLP

(57) ABSTRACT

A method for analyzing single cells by mass spectrometry includes the steps of providing a plurality of cells in a liquid medium and placing the cells and liquid medium in a single cell isolation and ejection system. Liquid medium containing a single cell is released from the single cell isolation and ejection system. The liquid medium and single cell are captured in a capture probe containing a flowing capture probe solvent. The cell is lysed by a lysis inducer in the capture probe to disperse single cell components into the medium. The lysed single cell components are transported to a mass spectrometer, where the lysed single cell components entering the mass spectrometer are spatially and temporally separated from any dispersed components of another single cell from the sample entering the mass spectrometer. Mass spectrometry is conducted on the lysed single-cell components. A system for analyzing single cells by mass spectrometry is also disclosed.

11 Claims, 22 Drawing Sheets

(56) References Cited

U.S. PATENT DOCUMENTS

2019/0339173 A1   11/2019  Kertesz et al.

OTHER PUBLICATIONS

Cahill et al.: "Absolute Quantitation of Propranolol from Spatially Distinct 20-and 40-mu m Dissections of Brain, Liver, and Kidney Thin Tissue Sections by Laser Microdissection-Liquid Vortex Capture-Mass Spectrometry", Analytical Chemistry 2016, 88(11), 6026-6034.
Gross et al.: "Single-Cell Printer: Automated, On Demand, and Label Free", Jala-J Lab Autom 2013, 18(6), 504-518.
Riba et al.: "Molecular Genetic Characterization of Individual Cancer Cells Isolated via Single-Cell Printing", Plos One 2016, 11(9).
Riba et al.: "Label-free isolation and deposition of single bacterial cells from heterogenous samples for clonal culturing", Sci Rep-Uk2016, 6.
International Search Report dated Jan. 31, 2020 in PCT/US19/61802.
Cahill John F. et al: "Automated Optically Guided System for Chemical Analysis of Single Plant and Algae Cells Using Laser Microdissection/Liquid Vortex Capture/Mass Spectrometry", Frontiers in Plant Science, vol. 9, Aug. 20, 2018 (Aug. 20, 2018), pp. 1-8.
Extended European Search Report dated Sep. 1, 2022 in 19899322.2.

RAPID NATIVE SINGLE CELL MASS SPECTROMETRY

CROSS-REFERENCE TO RELATED APPLICATIONS

This application claims priority to U.S. Provisional Patent Application No. 62/781,048 filed on Dec. 18, 2018, entitled "Rapid Native Single Cell Mass Spectrometry", the entire disclosure of which is incorporated herein by reference.

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in this invention.

FIELD OF THE INVENTION

The present invention relates generally to mass spectrometry, and more particularly to single cell mass spectrometry.

BACKGROUND OF THE INVENTION

Cell-to-cell differences are present in any cell population and, until recently, understanding of cell mechanisms relied on measure of cell populations in bulk. It is now generally understood that ensemble averages may not represent individual cell function, hence the need for single cell resolution in genomics, epigenomics, transcriptomics, proteomics and metabolomics. Recent developments in single cell DNA and RNA sequencing have enabled the remarkable ability to monitor cellular lineage and cellular heterogeneity with single cell resolution. However, even isogeneic cells, having an identical genotype, can exhibit stochastic cellular heterogeneity. Non-genetic cellular differences in the concentrations of metabolites and other components influence cell death susceptibility, kinetics and even the mode of death in response to uniform lethal drug exposure. In cancer treatment sequential rounds of cytotoxic chemotherapies often kill a constant fraction of cells in a tumor rather than an absolute number, suggesting either pre-existing cellular heterogeneity inhibiting treatment or the selective response of a cellular sub-population to the treatment. Regardless, non-genetic cellular heterogeneity has clear ramifications on treatment and overall efficacy of therapeutics.

Detection of metabolites with single cell resolution is a significant analytical challenge. Within a cell there are thousands of unique chemical species present at low concentrations that can change rapidly. Unlike with single cell genomics and transcriptomics, there are no amplification strategies available for metabolites, thus high sensitivity is required. Also critical is high single cell sampling throughput, which is needed to obtain enough single cell data to statistically distinguish differences between cellular populations or subpopulations. Flow cytometry, one of the most commonly used single cell measurement techniques, uses fluorescence-based molecular probes to analyze specific metabolites with extremely high throughput on the order of thousands of cells/s but, due to overlapping spectroscopic signatures, flow cytometry can only measure around a dozen molecules simultaneously. Mass cytometry can target up to 48 different molecular components using a combination of heavy-metal isotope-based molecular probes, but this still represents only a small fraction of the metabolites present in a single cell. Unfortunately, untargeted molecular analysis by flow and mass cytometry is not feasible because the researcher must know and select what molecules to investigate a priori.

Mass spectrometry (MS) is one of the most amenable technologies for untargeted single cell analysis due to its high sensitivity, chemical specificity and speed. Several vacuum and probe-based MS techniques have been developed to enable comprehensive, untargeted chemical analysis of single cells. Vacuum-based techniques include secondary ion MS (SIMS), matrix assisted laser/desorption ionization (MALDI), and laser/desorption ionization (LDI) techniques, which, while extremely sensitive, require significant modification of the cell outside of its natural state, such as fixation and dehydration, to facilitate analysis under vacuum. Several approaches, including live single cell MS, the single-probe MS and others, use manually guided probes such as pipettes, optical fibers and capillaries to measure cellular chemistry in situ and sometimes in vivo by ambient MS. However, low sampling throughput has limited the value of most of these methods as the measure of each cell can take an hour or more and requires significant user skill. A subset of ambient MS techniques use laser pulses to dissect single cells. These techniques are particularly useful for sampling cells in tissue. However, few of these techniques can measure cells from cell suspension and typically have low sampling throughput and sensitivity.

MS-based techniques could, with further development, form the basis of the technology required for rapid, quantitative and untargeted single cell chemical analysis. However, routine, quantitative measure of single cell chemistry is still challenging. Moreover, current MS platforms require extensive sample preparation procedures or otherwise perturb cells from their native state in order to facilitate analysis, which can have unforeseen ramifications on cellular chemistry. Chemical analysis of individual cells is a significant analytical challenge. Molecular concentrations are low and high sampling throughput is needed to obtain enough single cell data to statistically distinguish differences between cell populations or subpopulations. Single cell DNA and RNA sequencing using next generation sequencing technology can take 2-3 days and thousands of dollars for each experiment, though recent advances are beginning to make these techniques faster. Flow cytometry has been heavily used for high throughput single cell analysis over the last several decades. Unfortunately, molecular information obtained by flow cytometry is limited by the use of fluorescence-based molecular probes that can target only one or a few molecular features simultaneously in an experiment due to overlapping spectroscopic signatures. Mass cytometry (a combination of flow cytometry and inductively coupled plasma-mass spectrometry (ICP-MS)) has enabled up to 40 different components to be measured simultaneously in a single cell by using heavy-metal isotope-based molecular probes. Fluorescence-based flow cytometry and mass cytometry techniques are among the highest throughput technologies for measuring single cell chemistry and are capable of measuring thousands and hundreds of cells/s, respectively. However, untargeted molecular analysis is not feasible, i.e., the researcher must know and select what molecules to investigate a priori. Since cellular chemistry is complex, reactions can often proceed in an unanticipated manner and, thus, untargeted chemical analysis can provide critical insights. The addition of molecular probes also necessarily influences chemical makeup of the cell, which may have unknown ramifications on cellular chemistry.

The high sensitivity, chemical specificity and speed of mass spectrometry (MS) make it one of the most amenable technologies to use for single cell analysis. Several MS-based techniques have been developed to enable more comprehensive and untargeted chemical analysis of single cells, including the aforementioned mass cytometry technique. Nanomanipulation-based techniques are among the most sensitive and can measure cellular chemistry in situ. In these approaches cell contents are manually extracted via a nanopipette and directly analyzed by MS; however, low sampling throughput has limited the value of these methods as the measure of each cell can take the better part of an hour or more and requires significant user skill. Using laser ablation (LA)-MS systems, metabolic analysis can be achieved in a more rapid fashion, but of these techniques most have only measured major chemical constituents from large 70×400 µm single cells that do not represent the size of the majority of mammalian cells. Liquid vortex capture (LVC)-MS can measure cells with a throughput of ~15 s/cell, but the technique requires cells to be dried onto a microscope slide, a process which may distort the chemistry of the cell in unknown ways. Another LA-MS technique, matrix assisted laser desorption/ionization-MS (MALDI-MS), combined with microfluidic chips that gently trap single cells on a surface has high throughput (1-5 cells/s) and sensitivity for single cell analyses, however, intense matrix signals in the ≤500 mass per charge (m/z) range may interfere with small metabolites and pharmacological compounds of interest. Additionally, the application of matrix and other sample preparation processes are time-intensive, costly, and may alter cellular chemistry from its native state.

Currently available mass spectrometric analysis techniques are not yet capable of routinely and rapidly acquiring quantitative molecular information at the cellular level for a wide range of compound types (from small drugs and metabolites to large biopolymers like proteins). Moreover, many MS platforms require extensive sample preparation procedures or otherwise perturb cells from their native state in order to facilitate analysis, which can have unforeseen ramifications on cellular chemistry.

SUMMARY OF THE INVENTION

A method for analyzing single cells by mass spectrometry from a sample containing a plurality of cells includes the steps of providing a plurality of cells and a liquid medium and placing the cells and liquid medium in a single cell isolation and ejection system. The liquid medium containing a single cell is released from the single cell isolation and ejection system. The liquid medium and single cell are captured in a capture probe containing a flowing capture probe solvent. The cell is lysed with a lysis inducer in the capture probe to disperse single cell components into the medium. The lysed single cell components are transported to a mass spectrometer, where the lysed single cell components entering the mass spectrometer are spatially and temporally separated from any dispersed components of another single cell from the sample entering the mass spectrometer. Mass spectrometry can then be conducted on the lysed single cell components.

The lysis can be induced by a capture probe solvent providing a lower partial pressure than the internal pressure of the cell to cause lysis of the cell. The capture probe solvent can include at least one selected from the group consisting of methanol, ethanol, isopropranol, hexane, chloroform, dichloromethane, acetonitrile, and water.

The lysis can be induced by a chemical lysing agent. The chemical lysing agent can include at least one selected from the group consisting of sodium dodecyl sulfate (SDS), Triton-X, NP-40 lysis buffer, RIPA lysis buffer, Tween lysis buffer, CHAPS lysis buffer, and perfluorooctanoic acid.

The lysis can be induced by a liquid vortex formed by the flowing capture probe solvent. The liquid vortex fluid rate can be 50-300 µL/min and can have a 0.5-20 second elution time. The liquid vortex can be formed by a coaxial probe.

The lysis can be induced by a voltage applied across the cell in the capture probe solvent. The lysis can be induced by the application of 0.2-1.5 volts across the cell for 1-10,000 µs to the cell in the capture probe solvent.

The lysis can be induced by an acoustic wave emitted at the cell in the capture probe solvent. The lysis can be induced by an acoustic wave emitted at the cell in the capture probe having a frequency of 15-20 kHz for 0.1-10 seconds.

The release rate of the single cell isolation and ejection system can be from 0.1 cell/s to 100 cells/s. The release rate of the single cell isolation and ejection system can be drop on demand. The liquid medium can include a cell culture medium.

A system for analyzing single cells by mass spectrometry can include a single cell isolation and ejection system including a storage container for sample including a plurality of cells in a liquid medium. A capture probe can include at least one solvent supply conduit for flowing a capture probe solvent, a capture probe exhaust conduit for receiving single cells released by the single cell isolation and ejection system and conducting lysed cell components and capture probe solvent to a mass spectrometer, and a lysis inducer. The system can further include a mass spectrometer having an inlet connected to the capture probe exhaust conduit.

The lysis inducer can include a capture probe solvent. The capture probe solvent provides a lower partial pressure than the internal pressure of the cell to cause disruption of the cell. The lysis inducer can include a liquid vortex formed by the flowing capture probe solvent through the capture probe. A co-axial probe can include a liquid supply and an exhaust conduit for forming a liquid vortex by the flowing capture probe solvent. The lysis inducer can include electrodes arranged on two sides of the sampling capillary for applying a high voltage to cells in the capture probe. The lysis inducer can include a chemical lysing agent injector. The lysis inducer can include an acoustic wave generator located around the outside of the sampling capillary for applying an acoustic wave to cells in the capture probe.

BRIEF DESCRIPTION OF THE DRAWINGS

There are shown in the drawings embodiments that are presently preferred it being understood that the invention is not limited to the arrangements and instrumentalities shown, wherein.

DETAILED DESCRIPTION OF THE INVENTION

Figures 1A, 1B:
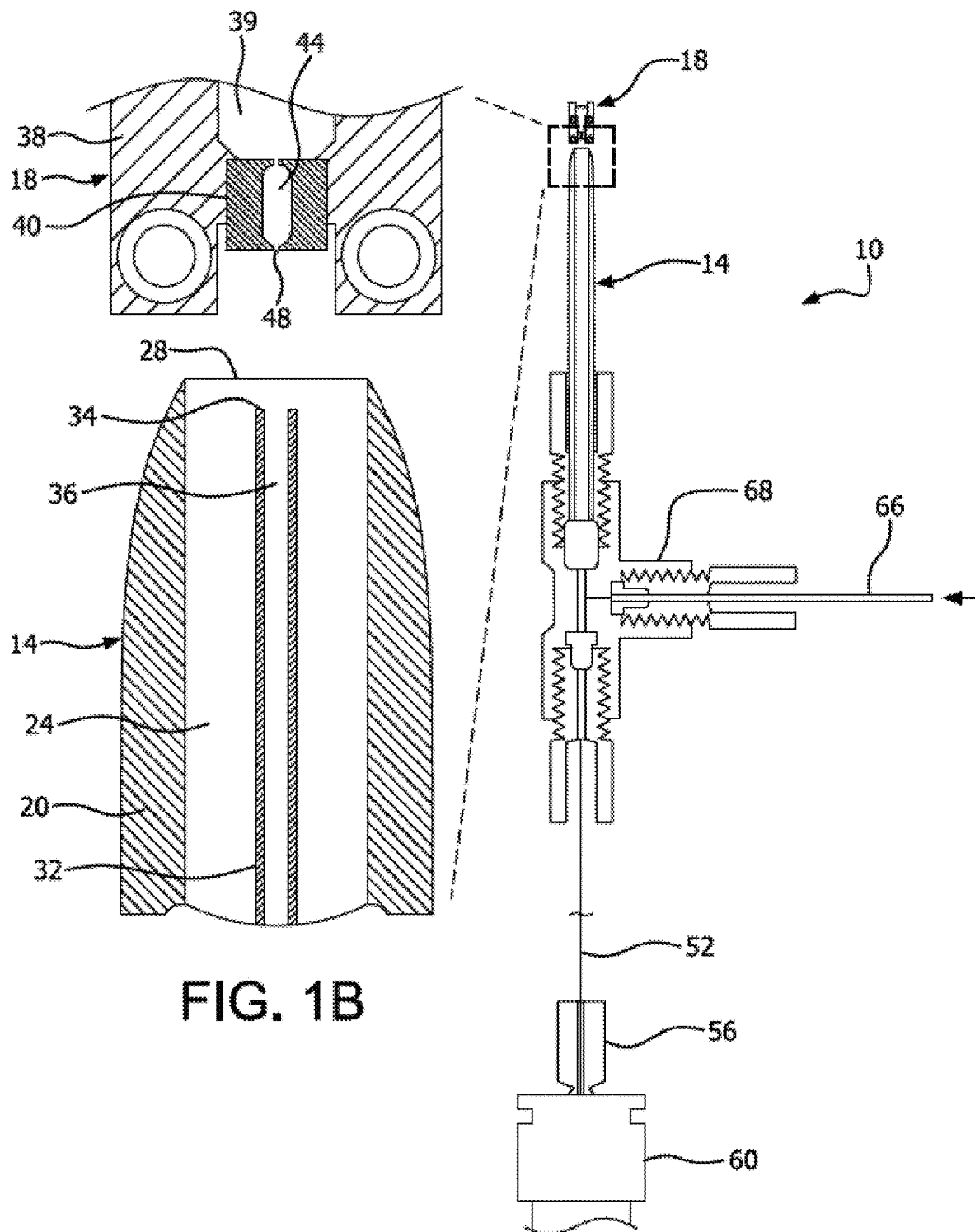
FIG. 1A is a schematic cross section of a system for analyzing single cells by mass spectrometry.
FIG. 1B is a magnified schematic cross section of a capture probe and single cell isolation and ejection system.

A method for analyzing single cells by mass spectrometry from a sample containing a plurality of cells includes the steps of providing a plurality of cells in a liquid medium and placing the cells and liquid medium in a single cell isolation and ejection system. Liquid medium containing a single cell is released from the single cell isolation and ejection system. The liquid medium and single cell are then captured in a capture probe containing a flowing capture probe solvent. The cell is lysed in the capture probe to disperse single cell components into the medium. The lysed single cell components are transported to a mass spectrometer, where the lysed single cell components entering the mass spectrometer are spatially and temporally separated from any lysed single cell of another cell from the sample entering the mass spectrometer. Mass spectrometry is conducted on the lysed single cell components. The lysis can be induced in the capture probe by different methods and structures.

A system for analyzing single cells by mass spectrometry can include a single cell isolation and ejection system including a storage container for a sample including a plurality of cells in a liquid medium. A capture probe includes at least one solvent supply conduit for flowing a capture probe solvent, a capture probe exhaust conduit for receiving single cells released by the single cell isolation and ejection system and conducting lysed cell components and capture probe solvent to a mass spectrometer, and a lysis inducer. The system can further include a mass spectrometer having an inlet connected to the capture probe exhaust conduit. The lysis inducer can vary. More than one type of lysis inducer can be incorporated into the capture probe.

The lysis inducer can include an appropriate capture probe solvent. The capture probe solvent provides a lower partial pressure than the internal pressure of the cell. The lysis is induced by the capture probe solvent providing a lower partial pressure than the internal pressure of the cell to cause disruption and lysis of the cell. The capture probe solvent can be any suitable solvent. The capture probe solvent can include at least one selected from the group consisting of methanol, ethanol, isopropanol, hexane, chloroform, dichloromethane, acetonitrile and water.

The lysis inducer can include a chemical lysing agent. The chemical lysing agent can be any suitable lysing agent. The chemical lysing agent can include at least one selected from the group consisting of sodium dodecyl sulfate (SDS), Triton-X, NP-40 lysis buffer, RIPA lysis buffer, Tween lysis buffer, CHAPS lysis buffer, and perfluorooctanoic acid. The chemical lysing agent can be dispersed in the capture probe solvent. The lysis inducer can include a chemical lysing agent injector. The position and construction of the chemical lysing agent injector can vary.

The lysis can be induced by a liquid vortex formed by the flowing capture probe solvent. The lysis inducer can include structure for forming the liquid vortex from the flowing capture probe solvent through the capture probe. The lysing vortex can be created by any suitable structure. The liquid vortex can be formed by a coaxial probe in which capture probe solvent flows from one coaxial solvent supply flow path, overflows a common open end, and enters the coaxial solvent exhaust flow path in a vortex flow pattern. Other vortex inducing structure in the exhaust flow path is possible. The coaxial probe can include a liquid supply and an exhaust conduit for forming a liquid vortex formed by the flowing capture probe solvent. The liquid vortex so created can have varying characteristics, but in general should provide sufficient kinetic energy to lyse the cell. The liquid vortex can have a fluid flow rate of 50-300 µL/min. The liquid vortex can have a fluid flow rate of 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295 and 300 µL/min, or within a range of any high value and low value selected from these values. The liquid of the capture probe solvent can have an elution time of 0.5-20 seconds. The liquid of the capture probe solvent can have an elution time of 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20 seconds, or within a range of any high value and low value selected from these values.

The lysis inducer can include electrodes arranged on two sides of the sampling capillary for applying a high voltage to cells in the capture probe. The lysis is induced by the application of the voltage to the capture probe solvent carrying the cell. The construction of the electrodes can vary, and the voltage applied can vary. The voltage can be 0.2-1.5 volts across the cell. The voltage can be 0.2, 0.3, 0.4, 0.5, 0.6, 0.7, 0.8, 0.9, 1.0, 1.1, 1.2, 1.3, 1.4, and 1.5 volts, or within a range of any high value and low value selected from these values. The time that the voltage is applied can vary. The voltage can be applied to the cell in the capture probe solvent for 1-10,000 µs. The voltage can be applied to the cell in the capture probe solvent for 1, 10, 20, 30, 40, 50, 60, 70, 80, 90, 100, 110, 120, 130, 140, 150, 160, 170, 180, 190, 200, 210, 220, 230, 240, 250, 300, 400, 500, 600, 700, 800, 900, 1000, 2000, 3000, 4000, 5000, 6000, 7000, 8000, 9000, or 10000 µs, or within a range of any high value or low value selected from these values.

The lysis inducer can include an acoustic wave generator located around the outside of the sampling capillary for applying an acoustic wave to cells in the capture probe. The lysis is induced by the acoustic wave emitted at the cell in the capture probe. The construction of the acoustic wave generator can vary. The frequency of the acoustic wave can vary. The acoustic wave can have a frequency that is near the resonant frequency of the cell membrane. The acoustic wave can have a frequency of 15-20 kHz. The acoustic wave can have a frequency of 15, 15.5, 16, 16.5, 17, 17.5, 18, 18.5, 19, 19.5 or 20 kHz, or within a range of any high value and low value selected from these values. The amount of time that the acoustic wave is applied to the cell can vary. The acoustic energy can be applied to the cell for 0.1-10 seconds. The acoustic energy can be applied to the cell for 0.1, 0.5, 1, 1.5, 2, 2.5, 3, 3.5, 4, 4.5, 5, 5.5, 6, 6.5, 7, 7.5, 8, 8.5, 9, 9.5 or 10 seconds, or within a range of any high value and low value selected from these values.

The release rate of the cells from the single cell isolation and ejection system can vary. The release rate of the single cell isolation and ejection system can be from 0.1 cell/s to 100 cells/s. The release rate of the single cell isolation and ejection system can be 0.1, 1, 10, 20 30, 40, 50, 60, 70, 80, 90, and 100 cell/s, or within a range of any high value and low value selected from these values. The release rate of the single cell isolation and ejection system is drop on demand. The liquid medium comprises a cell culture medium. The design and construction of the single cell isolation and ejection system can vary.

Droplet ejection using an inkjet printer-like mechanism as the single cell isolation and ejection device is an efficient means for isolation of single cells from bulk in a label free and non-contact manner and can utilize a microfluidic dispenser chip and a piezoelectric actuator that can be activated on demand. Once activated, the piezoelectric actuator compresses the dispenser chip causing release of a single droplet. The size of the ejected droplet (tuned to be slightly larger than a typical cell) and use of video microscopy to visualize cells in the microfluidic dispenser chip before they are ejected ensure that each droplet contains one cell. Cells remain viable after the droplet ejection process and these techniques are often used to populate new cell cultures stemming from a single genetic variant. The invention uses the single cell isolation and ejection technology, such as a single cell printer (SCP), to isolate and transfer single cells for analysis by mass spectrometry.

Liquid vortex capture (LVC) mass spectrometry or LVC-MS is a continuously flowing liquid solvent extraction, atmospheric pressure MS technology. The LVC-MS technique uses a co-axial tube design having a stable liquid vortex drain maintained at the sampling end of the probe when operated under optimized solvent and nebulizer gas conditions. Sample that comes in contact with the liquid vortex surface is captured, analyte molecules are extracted from the sample and transported to the ionization source of the mass spectrometer over a few seconds. Subsequently, the analyte is ionized using electrospray ionization (ESI), atmospheric pressure chemical ionization (APCI), or nearly any liquid-based ionization source and is detected by MS.

The single cell isolation and ejection system and capture probe lysis and MS technologies are coupled together by ejection of single cells directly into the lysis inducing capture probe. The droplet containing a single cell ejected by the single cell isolation and ejection system falls towards the capture probe, located directly below the site of droplet ejection. The droplet is captured by the flowing solvent of the capture probe where the cell is lysed by the lysis inducer. For example, upon being exposed to solvent (e.g., methanol, chloroform, etc.), the cell wall can rupture due to the change in osmotic pressure. The contents of the cell can be further extracted by the solvent while in transport to the ionization source of the mass spectrometer (~6 s). From there, the analyte molecules are ionized and then measured using MS in an untargeted (e.g., time-of-flight (TOF)-MS) or targeted (e.g., tandem MS) manner. The technique described in the invention is able to efficiently extract cellular contents while minimizing sample dilution, enabling the sensitivity needed to measure lipids and metabolites in single cells. Since the capture probe is continuously operating with flowing solvent, the probe is self-cleaning, and signal carryover from one cell to another is removed and background signal from solvent ions or ions due to media can be easily determined. Cells remain in their 'natural' state (i.e., in this case in growth media) until the point of lysis and chemical analysis by MS. Further, the technology requires no molecular labeling or other sample preparation protocols. The mass spectrometer and ionization source operate in the exact same manner as that of direct infusion-ESI experiments often used for measuring cell chemistry in aggregate.

FIG. 1A is a cross section of a system 10 for analyzing single cells by mass spectrometry. The system 10 includes a capture probe 14 and a single cell isolation and ejection system 18. The capture probe 14 can have differing dimensions. In the embodiment shown particularly in FIG. 1B, the capture probe 14 includes an outer tubular housing 20 having an open interior 24. The capture probe housing 20 includes an open end 28 communicating with the open interior 24. Within the open interior 24 is an exhaust conduit 32 having an open end 34 and an open interior 36. The dimensions and location of the exhaust conduit 32 can vary. In the embodiment shown, the exhaust conduit 32 is placed in substantially coaxial relationship with the outer housing 20. The open end 34 can be positioned within the open interior 24 in various locations, but in general will be offset from the open end 28 of the outer housing 20. This ensures that fluid flowing through the open interior 24 will be drawn into the open end 34 of the exhaust conduit 32.

Figure 2:
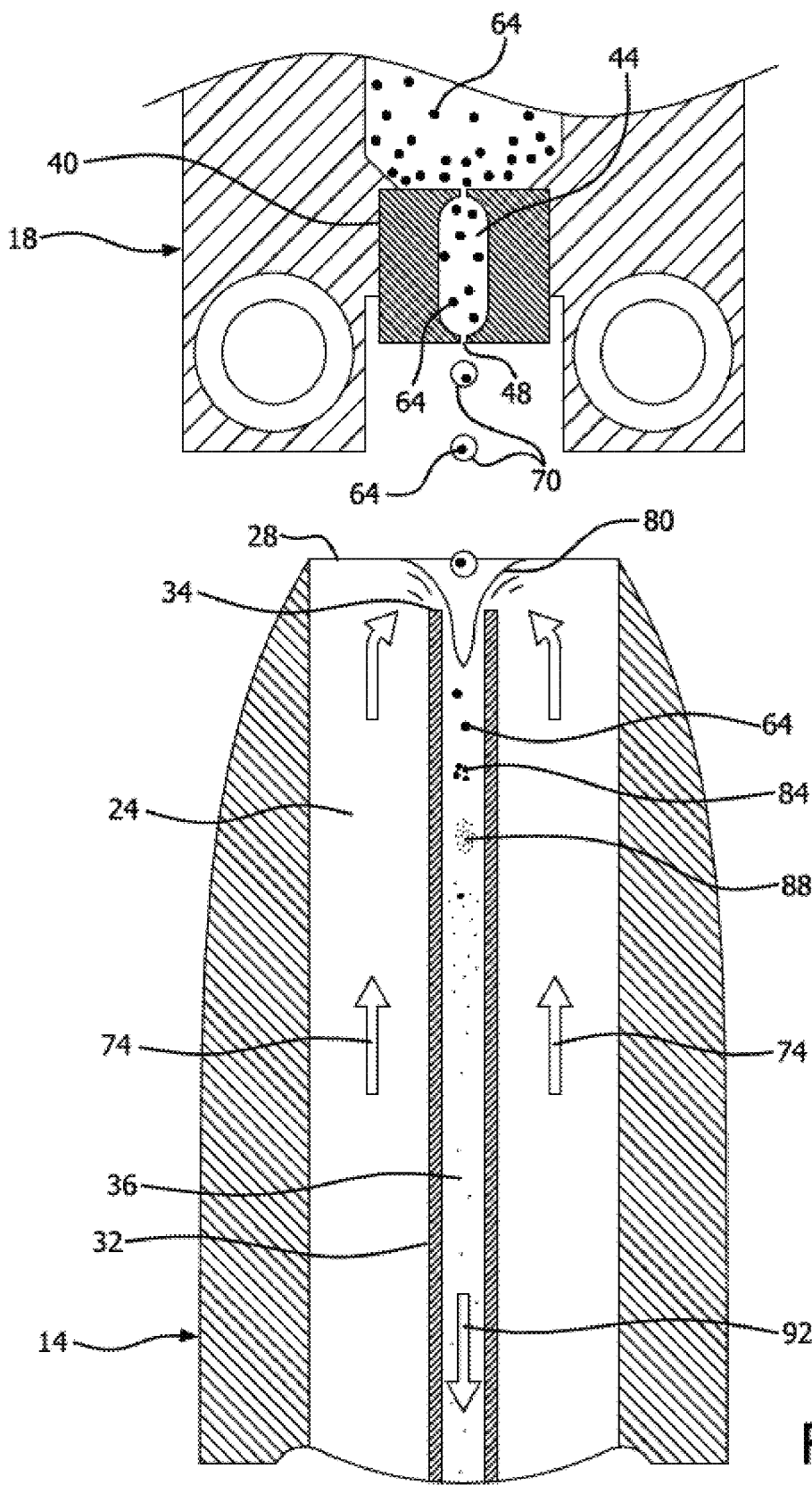
FIG. 2 is a magnified schematic cross section of a capture probe with a liquid vortex lysis inducer, and single cell isolation and ejection system.

The single cell isolation and ejection system 18 can have differing designs. Such devices are also known as single cell printers. In the embodiment shown, a housing 38 includes a container 39 for receiving a plurality of cells in a liquid medium. An isolation housing 40 includes an isolation chamber 44 that receives cells 64 and liquid medium from the container 39 (FIG. 2). An ejection opening 48 is dimensioned to pass single cells 64 in droplets of liquid medium 70.

Connections are provided to deliver solvent to the capture probe 14 and to remove solvent containing sample from the capture probe 14 and transport it to a mass spectrometer. The exhaust conduit 32 can communicate with mass spectrometer inlet conduit 52, attachment 56 and mass spectrometer port 60. A solvent inlet conduit 66 supplies solvent to the capture probe 14 and to the interior channel 24 of the capture probe housing 20. A manifold fitting 68 can be provided to conveniently provide connections and passage for the exhaust conduit 32, mass spectrometer inlet conduit 52, solvent inlet conduit 66, and capture probe housing 20. Other designs are possible.

The capture probe 14 includes a lysis inducer. The lysis inducer breaks up at least the cell wall or membrane of the single cell 64 when received from the single cell isolation and ejection system 18. The single cell 64 is received through the open end 28 of the capture probe 14. Solvent flows through the open interior 24 of the capture probe housing 20 in the direction shown by arrow 74 (FIG. 2) toward the open end 28 of the capture probe 14. A suitable pump can be applied to the exhaust conduit 32 to draw solvent into the open interior 36 of the exhaust conduit 32. Solvent will flow in the direction of arrow 92 from the capture probe to the mass spectrometer. The solvent flow rate in the open interior 24 can be balanced with the solvent flow rate in the open interior 36 such that solvent does not overflow the open end 28 of the capture probe housing 20. The single cell 64 enters the open end 28 of the capture probe 14 and is drawn into the open interior 36 of the exhaust conduit 32. The cell membrane of the single cell 64 is lysed by the lysis inducer as the single cell 64 traverses the exhaust conduit 32.

The manner in which the lysis inducer operates, and its position and construction, can vary. There is shown in FIG. 2 a solvent vortex 80 that operates as a lysis inducer. The solvent vortex 80 is created by the design and construction of the outer housing 20, exhaust conduit 32, and the relative flow rates in the open interior 24 and the open interior 36. The single cells 64 in droplets 70 of liquid medium enters the open end 34 of the exhaust conduit 32 and contacts the vortex 80. The kinetic energy of the vortex 80 breaks apart the single cell 64, at least the cell membrane. Cell pieces 84 are produced. It is also possible that the kinetic energy of the vortex 80 further breaks apart the cell pieces 84 into smaller cell fragments 88.

Figure 3:
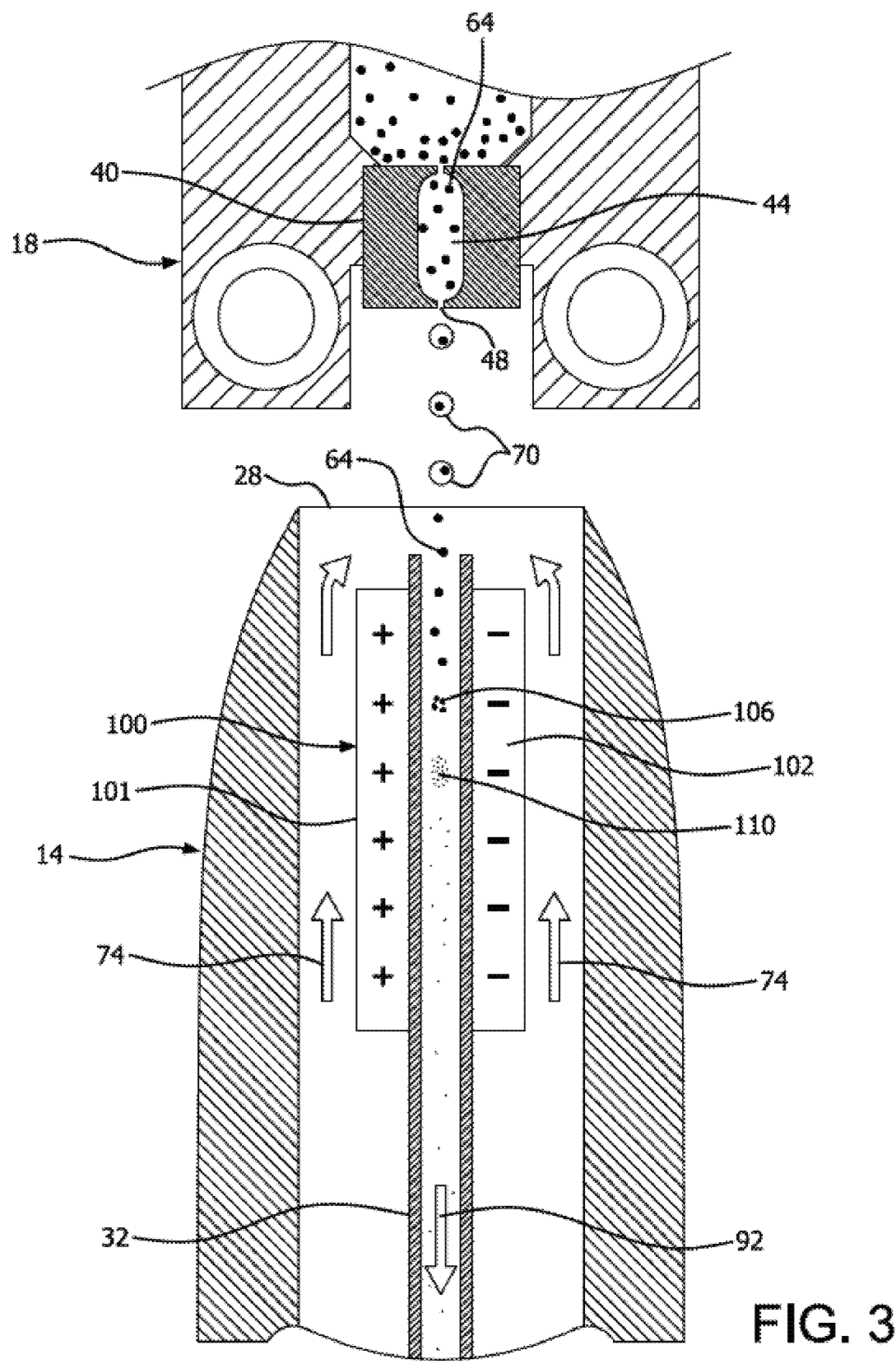
FIG. 3 is a magnified schematic cross section of a capture probe with an applied voltage lysis inducer, and single cell isolation and ejection system.

FIG. 3 is a magnified cross section of a capture probe with an applied voltage lysis inducer. The applied voltage license inducer 100 includes electrodes 101 and 102 which are positioned so as to induce a voltage potential across the solvent within the open interior 36 of the exhaust conduit 32. The electrodes 101 and 102 are shown within the capture probe 14 however, it is also possible to position the electrodes elsewhere in the capture probe 14 as within the outer housing 20 or outside the outer housing 20. The applied voltage will act on single cells 64 traversing the exhaust conduit 32 to break the cell membrane and create cell pieces 106, and possibly also cell fragments 110.

Figures 4A, 4B:
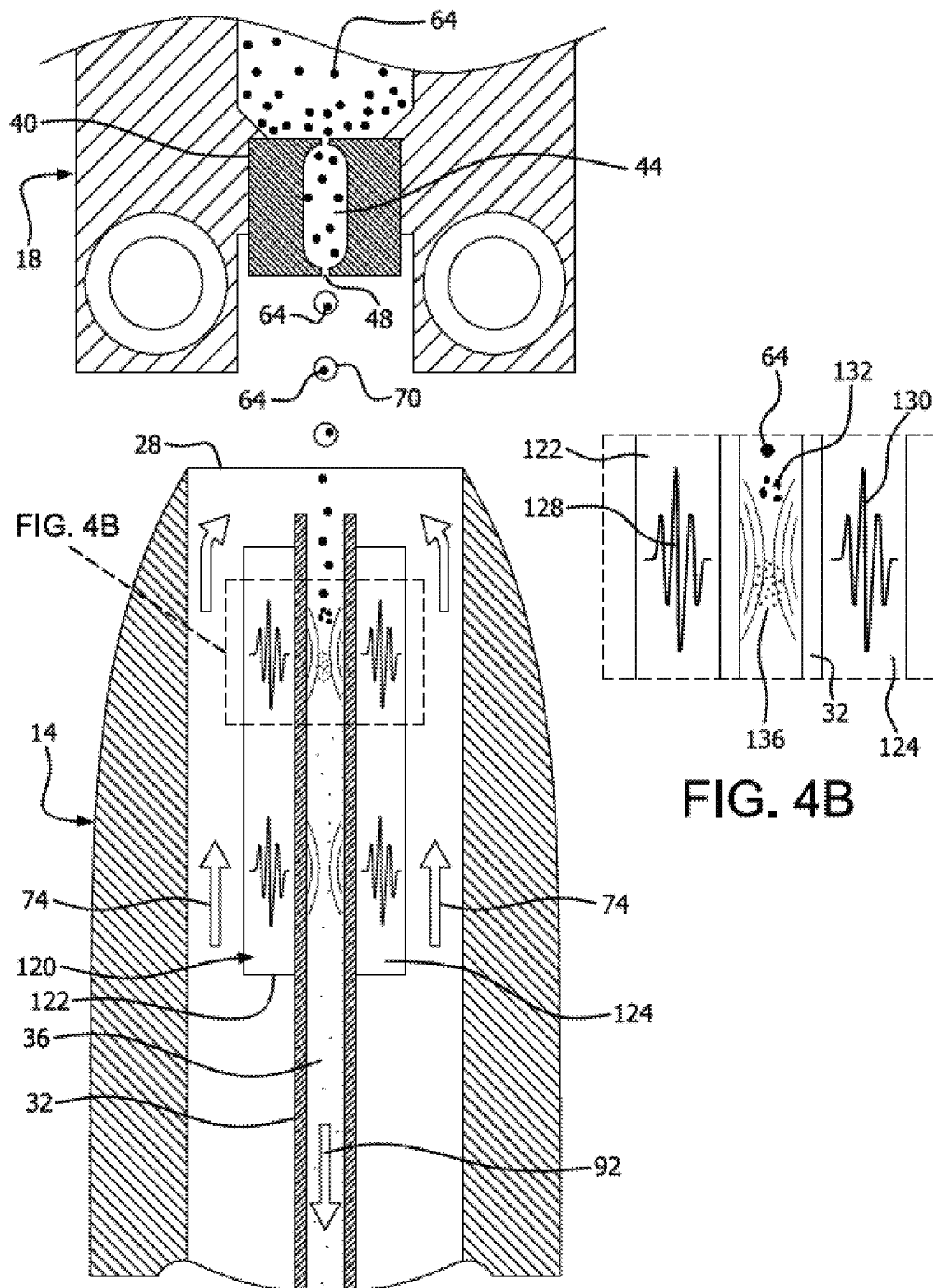
FIG. 4A is a magnified schematic cross section of a capture probe with an acoustic energy lysis inducer, and single cell isolation and ejection system.
FIG. 4B is a magnified schematic depiction of area FIG. 4B in FIG. 4A.

It is also possible to use acoustic energy as a lysis inducer. There is shown in FIG. 4A is a magnified cross section of a capture probe with an acoustic energy lysis inducer 120 that is comprised of an acoustic energy transducer 122 and possibly an additional acoustic energy transducer 124. Acoustic energy transducers are well-known and different sizes and shapes and locations are possible. As shown particularly in the expanded view of FIG. 4B, an acoustic wave 128 can be generated by transducer 122 and an acoustic wave 130 can be generated by transducer 124. The acoustic energy is transferred through the exhaust conduit 32 and in parts the acoustic wave to the solvent flowing through the exhaust conduit 32. The acoustic wave energy results in the single cell 64 being lysed into cell pieces 132 and possibly also cell fragments 136 as the single cell 64 traverses the exhaust conduit 32 and the acoustic wave energy.

Figure 5:
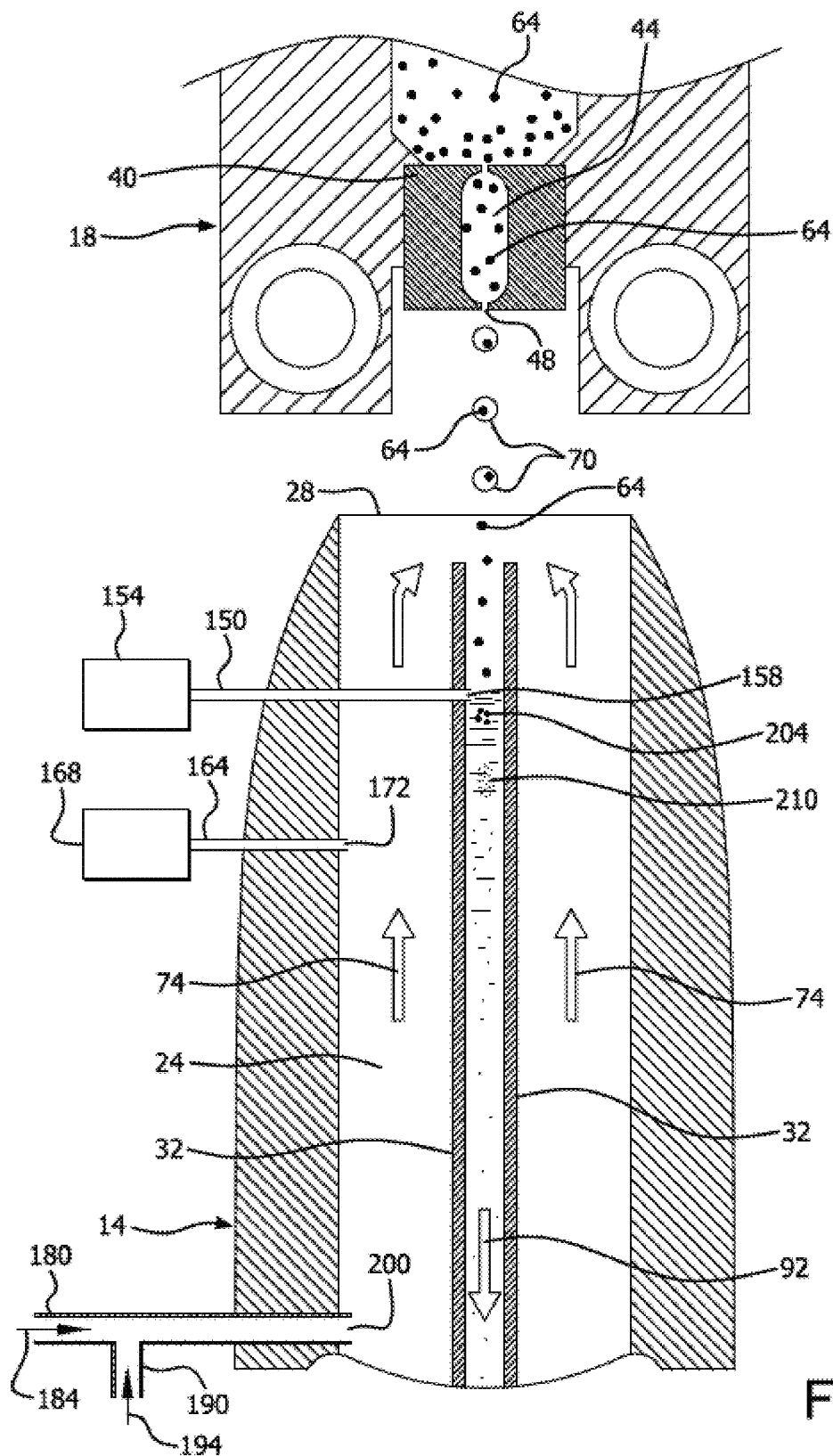
FIG. 5 is a magnified schematic cross section of a capture probe with a lysing agent injector, lysis inducer, and single cell isolation and ejection system.

The lysis inducer can also comprise a lysing agent. Lysing agents are chemical compositions which react with components of the cell wall or membrane to disrupt the cell membrane and release cellular components. The lysing agent may further act to degrade the cellular components into smaller cellular pieces and fragments. The lysing agent can be selected for this purpose. FIG. 5 is a magnified cross section of a capture probe 14 with a lysing agent injector. The precise construction and location of the lysing agent injector can vary, and different embodiments are shown in FIG. 5. A lysis agent injector 150 can receive lysing agent from source 154 and releases the lysing agent at opening 158 into the exhaust conduit 32. The lysing agent will contact the single cell 64 within the exhaust conduit 32 to lyse the cell 64 into cell pieces 204 and possibly cell fragments 210. Other lysing agent injectors are possible. A lysing agent injector 164 can receive lysing agent from source 168 and releases the lysing agent into the open interior 24 of housing 20 at an opening 172. It is also possible to inject the lysing agent into the solvent prior to the solvent reaching the capture probe 14. There is shown in FIG. 5 another alternative embodiment in which the solvent supply line 180 receives solvent flow stream 184. A lysing agent injector 190 receives lysing agent flow 194 and injects the lysing agent into the solvent flow stream 184. The combination of solvent and lysing agent is then injected at opening 200 into the open interior 24 of the housing 20, such that the lysing agent will contact cells 64.

The invention was tested using a single cell isolation and ejection system which incorporated small droplet piezoelectric ejection followed by capture of the droplet into a liquid vortex capture probe, cell lysis, and transport to the mass spectrometer. Once exposed to an appropriate solvent the cell is lysed, extracted and analyzed by MS. The method was validated by measuring the lipid composition of microalgae, *Chlamydomonas reinhardtii* (ChRe) and *Euglena gracilis* (EuGr), and HeLa cells in their native growth media. ChRe and EuGr microalgae mixed together in the same solution were able to be differentiated cell-by-cell based on measured lipid profiles. Numerous diacylglyceryltrimethylhomo-Ser (DGTS), phosphatidylcholine (PC), monogalactosyldiacylglycerol (MGDG) and digalactosyldiacylglycerol (DGDG) lipids were observed in single cells. Continuous solvent flow ensures that cells are analyzed rapidly and no signal carryover between cells is observed. ChRe and EuGr microalgae mixed together in the same solution were differentiated cell-by-cell in real-time based on differences between levels of diacylglyceryltrimethylhomo-Ser (DGTS) and phosphatidylcholine (PC) lipids measured in each cell. Several DGTS lipids present in ChRe were quantified with single cell resolution by normalizing lipid mass spectrometric signal to a DGTS(32:0) internal standard added to the LVC probe solvent during analysis. Quantitative peak areas were validated by comparing to bulk lipid extracts. Peak area distributions comprised of hundreds of cells were compared for ChRe after 5 days of nitrogen-limited and normal growth conditions, which show clear differences and the ability to resolve cellular population differences with single cell resolution. A total of >20,000 cells were analyzed in these experiments.

LC-MS CHROMASOLV® methanol+0.1% formic acid (FA), chloroform, and water were purchased from Sigma- Aldrich (St. Louis, Mo., USA). EuGr cells were purchased from Carolina Biological (Burlington, N.C., USA). ChRe CC-503 cw92 mt+ and CC-125 wild type mt+ [137c] were purchased from the Chlamydomonas Resource Center (St. Paul, Minn., USA). Algae was grown in high salt medium (HSM) media under constant shaking, light, and temperature (25° C.). In normal growth (+N) and nitrogen deprived (−N) ChRe growth experiments, cells were grown for 5 days under constant shaking, light, and temperature (25° C.) in HSM and HSM made without ammonium chloride, respectively. Cell counts were measured using a hemacytometer. HeLa cells were purchased from ATCC (Manassas, Va., USA). DGTS(32:0) was purchased from Avanti Polar Lipids (Alabaster, Ala., USA).

The system was comprised of a commercially available single cell isolation and ejection device, the Single-Cell Printer™ (Cytena GmbH, Freiburg, Germany) coupled with a modified sampling capture probe. The single cell isolation and ejection device is a benchtop sized, automated drop-on-demand cell printer utilizing the inkjet-like dispensing principle combined with optical microscopy to ensure one cell-per-droplet is ejected. Using this device >95% of ejected droplets contain a single cell. In practice, shadows along the wall of the microfluidic sample cartridge can obfuscate a cell from an image recognition algorithm potentially resulting in two cells in a droplet, thus, single cell dispensing efficiency is <100%. The instrument used in this study is capable of ejection of droplets at a controllable throughput of up to ~30 droplet/s and can isolate cells ranging in size between 5-30 µm diameter.

The single cell isolation and ejection system dispenser and image recognition settings need to be adjusted for each sample cartridge used and for the cells being investigated. For each experiment, a disposable microfluidic sample cartridge was filled with 50 µL of cell solution and was mounted onto the dispenser. The dispenser's piezo-electric plunger generates ~70 µm droplets in diameter from the cartridge without being in direct contact to the sample. A video monitor and image recognition algorithm detected cells in the droplet ejection area of the sample cartridge. Droplets not containing a single cell, or containing two or more cells, are removed using a vacuum shutter system located directly underneath the nozzle, while those droplets that do contain a single cell are allowed to pass. Once the sample cartridge is attached to the dispenser, the cell image recognition target area is set to the region surrounding the orifice of the sample cartridge. The image algorithm was tuned to accurately identify cells in the sample cartridge. A 5-25 µm cell diameter, 0.4-1.0 roundness and 30 greyscale thresholds were used for all experiments. The piezoelectric instroke depth (8-12 µm) and speed (90-110 µm/ms) were tuned to eject droplets reproducibly, evidenced by imaging of the droplets after ejection.

The capture probe consisted of a 1.12 mm i.d. 1.62 mm o.d. stainless steel outer annulus connected to a 5-port PEEK manifold (IDEX Health and Science). The inner annulus was a 20-cm long, 0.178 mm i.d., 0.794 mm o.d. PEEK capillary (IDEX Health and Science) that directly connected to the ion source of the mass spectrometer.

The single cell isolation and ejection system was placed on top of a Sciex TripleTOF® 5600+ mass spectrometer and the capture probe was attached onto the base of the single cell isolation and ejection system. The sample cartridge was aligned 1 mm directly above the capture probe, ensuring that all droplets ejected for analysis are captured by the probe. The capture probe solvent flowrate varied with solvent composition. Mass spectrometer scan settings were optimized for each experiment.

Single cell mass spectrometry data was analyzed using Matlab 2018b (Mathworks, Natick, Mass., USA). SCPAssistant v1.20© software was used for real-time cell differentiation and was written in Delphi 3. All mass spectra were background subtracted from spectra acquired from droplets containing just cellular media.

The event that a single droplet contains a cell is a Poisson point process such that the cell concentration and droplet ejection frequency (i.e., flow rate) are necessary to predicting the throughput of single cell droplet ejection by the SCP. A droplet ejection speed of 30 droplets/s was used which corresponds to a ~0.32 µL/min flow rate. Cell concentrations around $1 \cdot 10^6$ cells/mL generally yielded a high enough SCP speed to reach the throughput limitation of mass spectrometric analysis.

Figure 6:
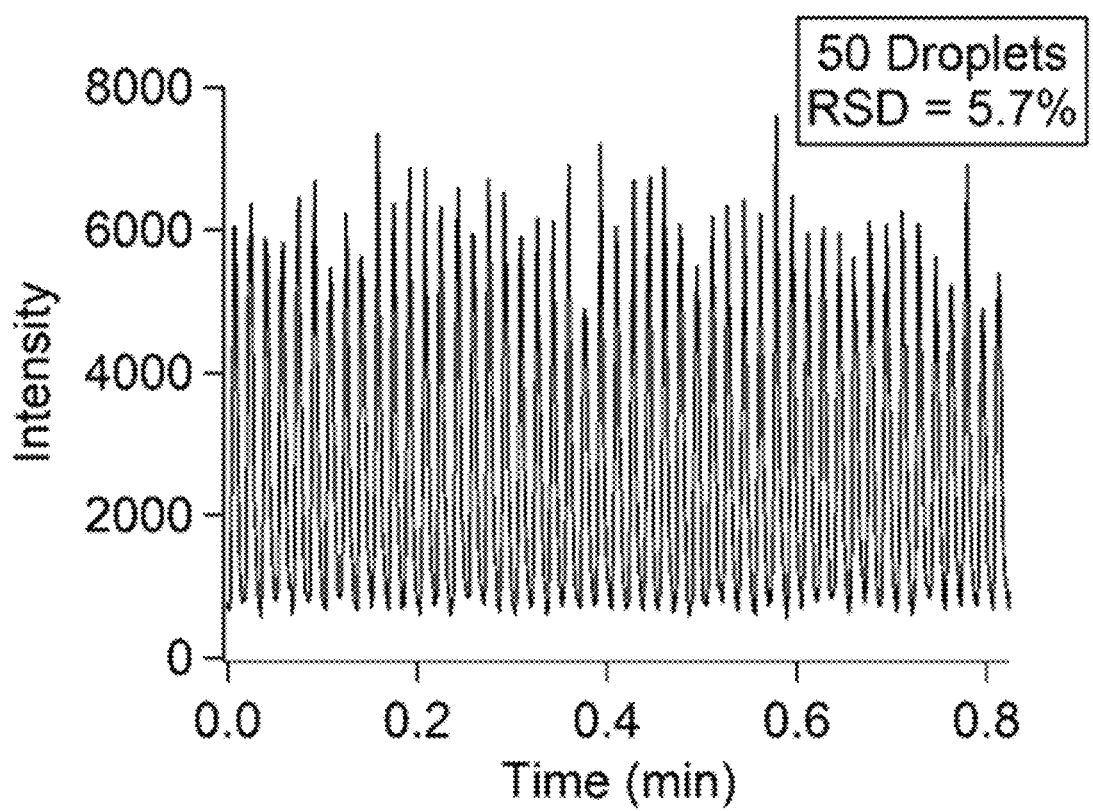
FIG. 6 is a plot of caffeine mass spectrometry signal intensity vs. Time (min) for caffeine droplets with a 90/10/0.1 (v/v/v) methanol/chloroform/formic acid solvent composition.

A 2.5 µM solution of caffeine dissolved in water was used to validate capture probe-droplet alignment and evaluate the analytical metrics of the system such as sensitivity, reproducibility, peak width, peak shape, and sampling throughput. The caffeine droplet experiments used a 150 µL/min flow rate with a 90/10/0.1 (v/v/v) methanol/chloroform/formic acid solvent composition. The capture of 50 consecutive droplets corresponding to 163 amol of caffeine/droplet spaced 1 s apart measured using single reaction monitoring (SRM) ESI-MS of caffeine (m/z 195.1 $[M+H]^+ \rightarrow$ 138.1 $[M-C_2NOH_3+H]^+$), 0.10 s accumulation time, 5500 V electrospray voltage (IS), 70 V declustering potential (DP), 27 eV collision energy (CE), 400° C. turbo heater temperature (TEM), and GS1=90 and GS2=60 $N_2$ gas settings. These tests resulted in reproducible peaks (RSD=5.7%) ~1.2 s wide (baseline-to-baseline, see FIG. 6). Continuous solvent flow ensures that there is no signal carryover between droplets, evidenced by a return to baseline solvent ion signals between droplets. Based on these metrics the maximum sampling throughput of this single cell printer/liquid vortex capture/mass spectrometry (SCP-LVC-MS) system would be ~1 cell/s.

To evaluate the ability of the system to measure single cell chemical profiles CC-125 wild type mt+[137c] ChRe microalgae which are ~5-15 µm in diameter were used. The ChRe cell suspension was pipetted, without dilution or other alteration to the cell suspension, into the single cell isolation and ejection system sample cartridge, placed on the dispenser and settings tuned for droplet ejection. Only droplets containing a single cell were allowed to fall into the capture probe. Images of the sample cartridge immediately before and after droplet ejection of a cell were taken and used to verify proper ejection. The signal peak width due to each cell was measured to be ~1.2 s, identical to droplets of caffeine measured previously and shown in FIG. 6. Multiple MS scans can be acquired within this duration. Dozens of discrete ions were observed in the TOF mass spectrum. Ions were predominantly diacylglyceryltrimethylhomo-Ser (DGTS) and monogalactosyldiacylglycerol (MGDG) lipids, based on separate tandem MS experiments and SWATH-MS scans which show an abundance of the DGTS headgroup and MGDG fragment ions. Specific lipids identified include DGTS(34:4) (m/z 732.6 $[M+H]^+$), DGTS(34:3) (m/z 734.6 $[M+H]^+$), DGTS(38:4) (m/z 783.5 $[M+H]^+$), MGDG(34:7) (m/z 767.5 $[M+Na]^+$) among other small molecules including pheophytin a (m/z 871.7 $[M+H]^+$), chlorophyll a (m/z 893.7 $[M+H]^+$) and chlorophyll b (m/z 906.7 $[M+H]^+$).

Separate experiments were conducted to validate that additional cell types, including mammalian cells, can be measured with the SCP-LVC-MS technique. Single cell mass spectra were acquired for an additional microalgae, EuGr, as well as for HeLa cells, the latter a commonly used human epithelial cell line derived from cervical cancer. Cell suspensions of each cell type were pipetted directly from their culture or storage medium (HSM and phosphate buffered saline (PBS) for microalgae and HeLa cells, respectively) into respective SCP sample cartridges and sampled by the LVC probe. Other than dilution of the HeLa cell suspension no sample preparation such as filtering, centrifugation, fixing was used in either experiment prior to analysis.

Single cell analysis of ChRe used a 150 µL/min flowrate with a 90/10/0.1 (v/v/v) methanol/chloroform/formic acid solvent composition. The mass spectrometer was configured to acquire TOF mass spectra (m/z 700-1000, 0.05 s accumulation time, IS=5500 V, DP=70 V, TEM=400° C., GS1=90 and GS2=60) as well as three SWATH mass spectra. The three SWATH-MS acquisition scan windows used in this experiment were SWATH spectra #1=m/z 700-800, SWATH spectra #2=m/z 800-900, and SWATH spectra #3=m/z 900-1000. A m/z 100-1000 scan range, 0.03 s accumulation time, IS=5500 V, DP=35 V, CE=48 eV, collision energy spread (CES)=15 eV, TEM=400° C., GS1=90 and GS2=60 nebulizer gas settings were used for each SWATH experiment. The TOF and three SWATH scans were acquired continuously every 0.2 s.

Figure 7:
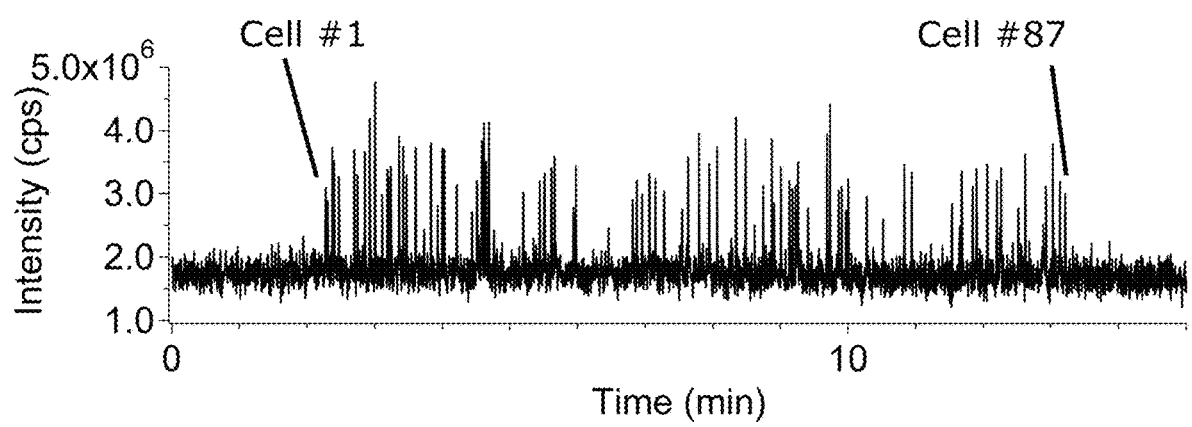
FIG. 7 is a plot of total mass spectrometry ion current (cps) vs. time (min) for *Euglena gracilis* cells.
Figure 8:
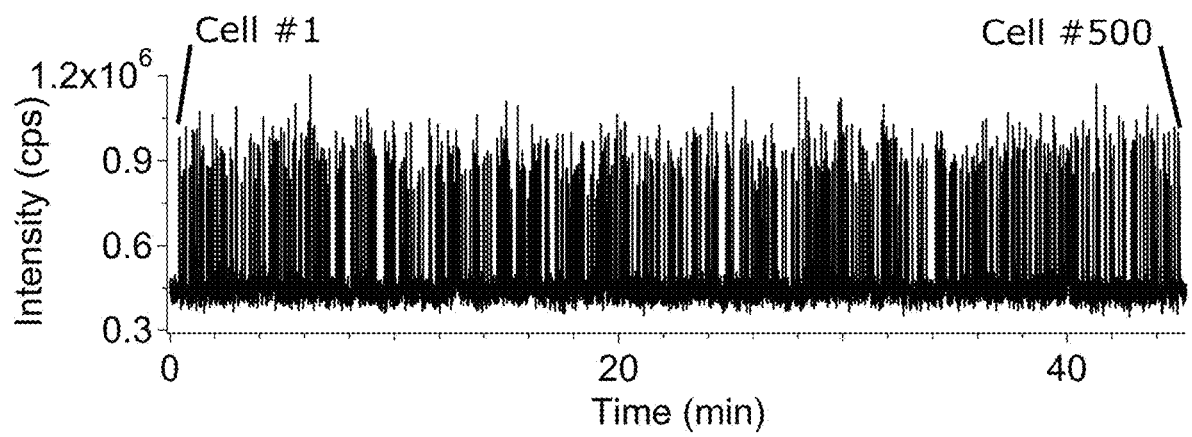
FIG. 8 is a plot of total mass spectrometry ion current (cps) vs. time (min) for HeLa cells.
Figure 9:
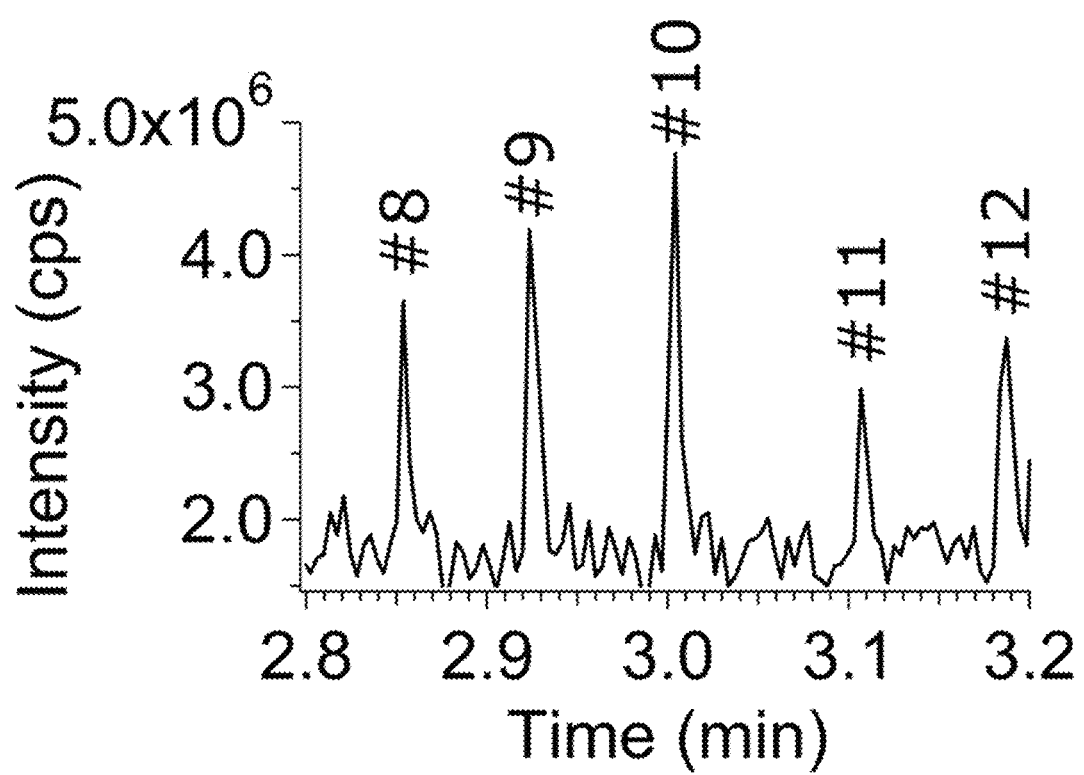
FIG. 9 is a zoomed plot of total mass spectrometry ion current (cps) vs. time (min) for *Euglena gracilis* cells.
Figure 10:
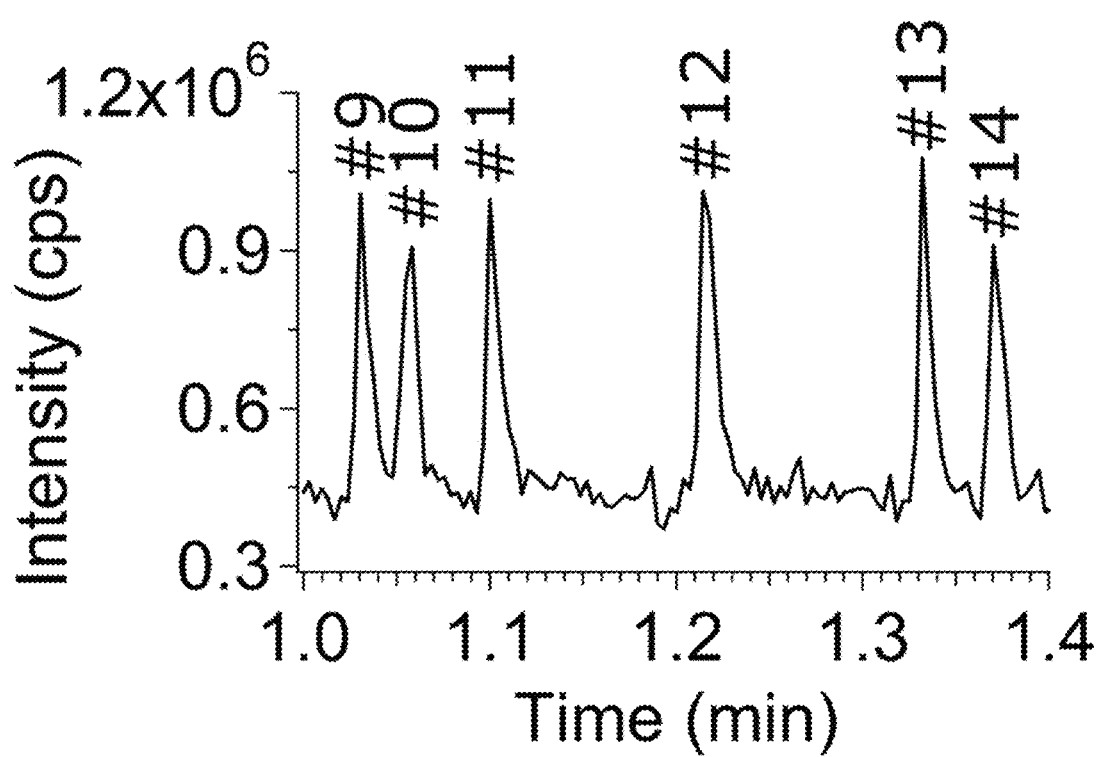
FIG. 10 is a zoomed plot of total mass spectrometry ion current (cps) vs. time (min) for HeLa cells.
Figure 11:
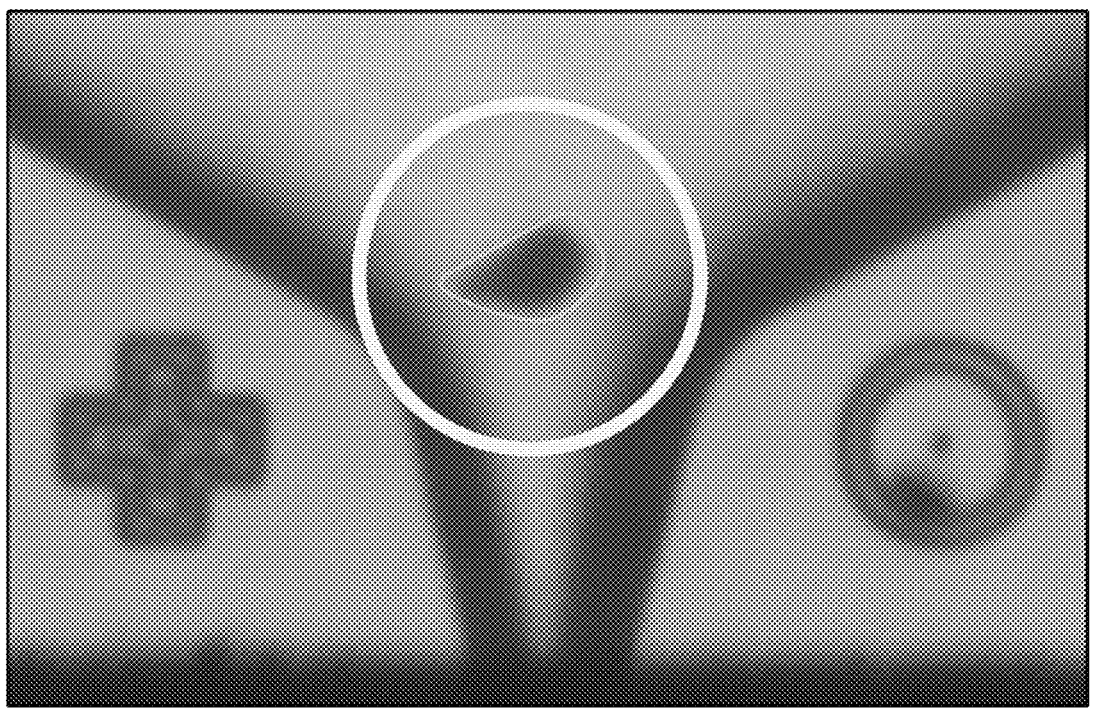
FIG. 11 is an image of a *Euglena gracilis* cell, before ejection.
Figure 12:
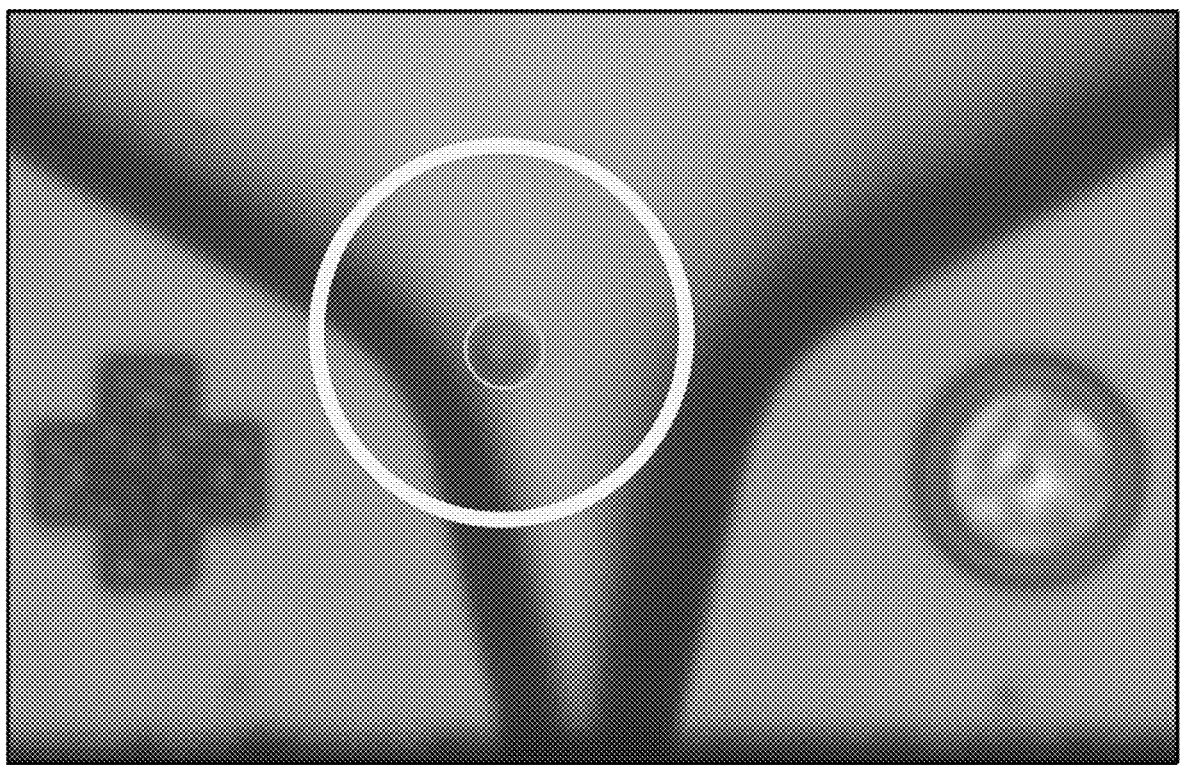
FIG. 12 is an image of a HeLa cell, before ejection.

Single cell analysis of EuGr and HeLa cells used a 150 µL/min flowrate with a 90/10/0.1 (v/v/v) methanol/chloroform/formic acid solvent composition. The mass spectrometer was configured to acquire TOF mass spectra (m/z 700-1000, 0.10 s accumulation time, IS=5500 V, DP=70 V, TEM=400° C., GS1=90 and GS2=60). The total ion chromatogram (TIC) of EuGr is shown in FIG. 7. The TIC of HeLa is shown in FIG. 8. FIG. 9 and FIG. 10 show zoomed views of the TIC traces for EuGr and HeLa experiments, respectively. Images of (d) EuGr and (e) HeLa cells before ejection are shown in FIG. 11 and FIG. 12, respectively, before ejection. EuGr cells are ~20 µm in diameter, are elliptically shaped and are highly mobile as evidenced by their movement in the sample cartridge during SCP-LVC-MS analysis. The activity of the cells highlight that they are unperturbed from their natural state up until the point of LVC probe capture.

Figure 13:
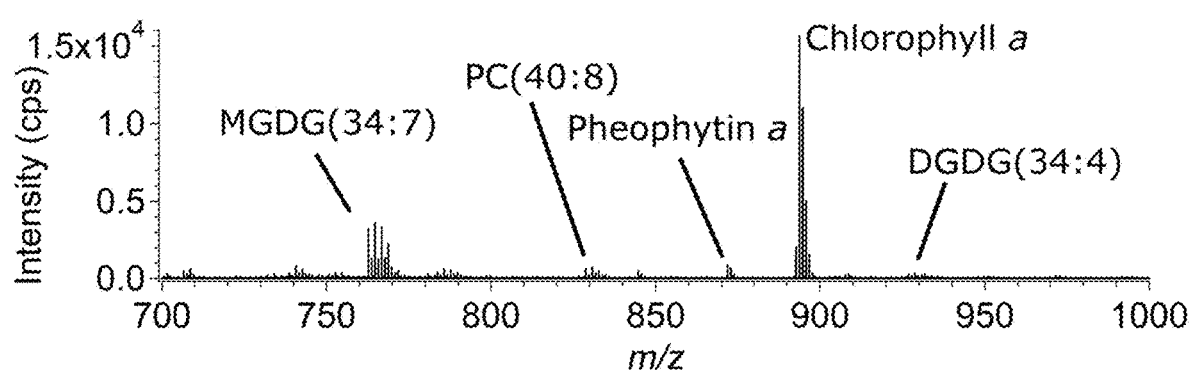
FIG. 13 is a mass spectral plot of intensity (cps) vs. mass-to-charge ratios (m/z) for a single *Euglena gracilis* cell.
Figure 14:
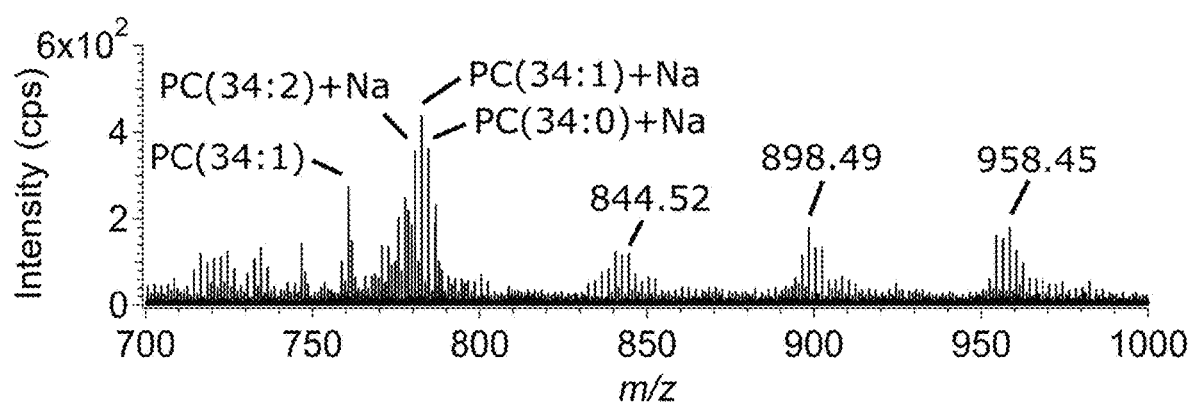
FIG. 14 is a mass spectral plot of intensity (cps) vs. m/z for a single HeLa cell.

Mass spectra of the EuGr are shown in FIG. 13, and for the HeLa cell in FIG. 14. TOF-MS spectra from EuGr cells (FIG. 13) contain ions similar to ChRe (such as pheophytin a, chlorophyll a and chlorophyll b). Most predominantly, MGDG(34:7) (m/z 762.7 [M+NH$_4$]$^+$), phosphatidylcholine (PC)(40:8) (m/z 830.6 [M+H]$^+$) and digalactosyldiacylglycerol (DGDG)(34:4) (m/z 930.6 [M+H]$^+$) lipids were observed. The image and mass spectrum of a single HeLa cell (~15 µm diameter) are shown in FIG. 12 and FIG. 14, respectively. 500 single cell mass spectra were acquired in one experiment. Identified ions include PC(34:1) (m/z 760.7 [M+H]$^+$), PC(34:2) (m/z 780.6 [M+Na]$^+$), PC(34:1) (m/z 782.6 [M+Na]$^+$) and PC(34:0) (m/z 784.6 [M+Na]$^+$) among many other ions that were unidentified.

Together this data highlights the capability to measure single cell chemistry from algae and mammalian cell types. No sample preparation measures were taken other than dilution, but, at most, cells may need to be diluted/concentrated or media filtered for large particulates to facilitate high sampling throughput and mitigate the potential for clogging of the SCP sample cartridge, respectively. The HSM and PBS media generally had a negligible effect on single cell mass spectra in this m/z range (700-1000) and could be evaluated by sampling empty droplets of each media. The small size of the droplet (70 µm) relative to the probe (1 mm) minimizes the impact of high salt-induced ion suppression effects, as has been seen in prior work. Measure of empty droplets yielded little to no signal of the lipids measured in the cells, indicating that lipid signal is from a cell lysed in the LVC probe rather than cellular exudates in solution.

Unique to the system is the ability to measure single cells in an untargeted manner with high sampling throughput relative to other untargeted MS single cell approaches. The acquisition of 1000 ChRe cells were taken with an overall sampling throughput of ~2.5 s/cell. The analyte signal from each cell was fully resolved baseline-to-baseline without cross contamination between cells. The theoretical throughput of the system is ~1 s/cell based on the ~1.2 s signal peak width of a single droplet containing caffeine. In practice, throughput is slower because cells are not aligned optimally in solution, as not every droplet contains a single cell and thus are removed by the vacuum shutter of the SCP.

Figure 15:
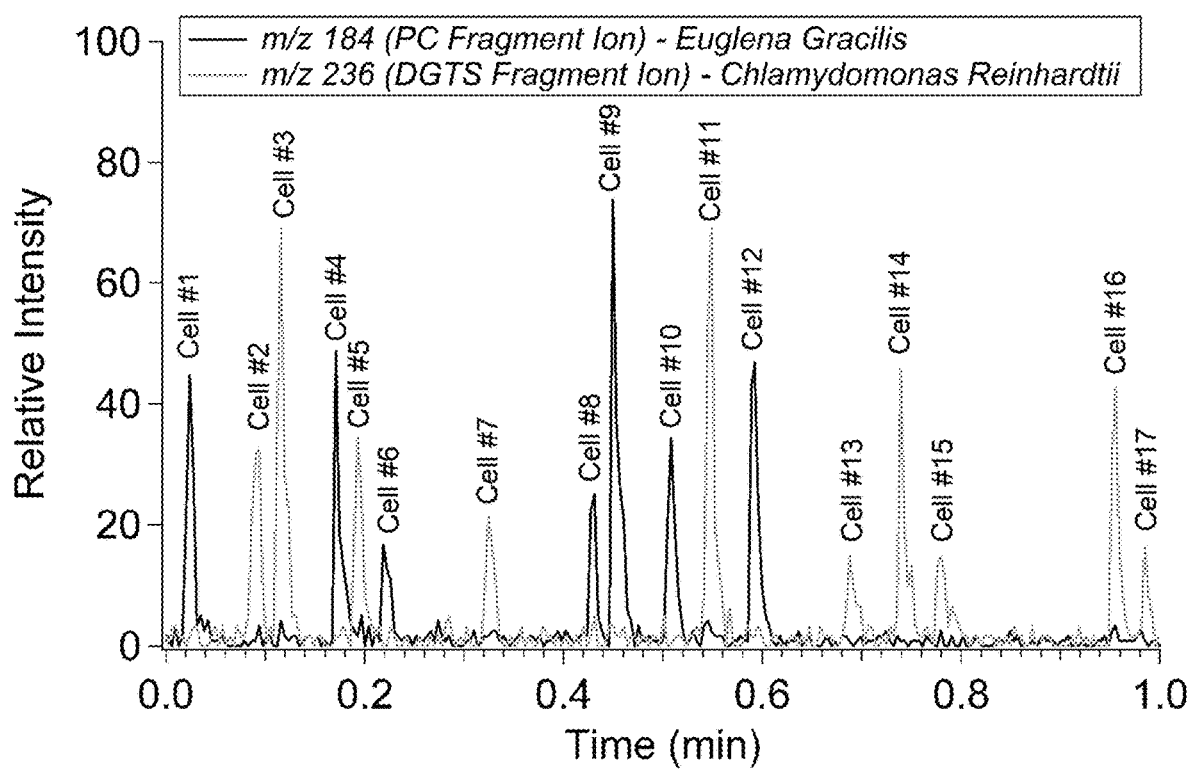
FIG. 15 is a plot of intensity vs. time (min) for m/z 184, a PC Fragment ion, *Euglena Gracilis*, and m/z 236, DGTS Fragment ion, *Chlamydomonas Reinhardtii*.

To demonstrate that a single cell is being measured in each droplet, (1:1 v/v) cell suspensions of ChRe were mixed with EuGr and single cell mass spectra were acquired. These two cell types can be chemically differentiated by the strong presence of DGTS lipids in ChRe and PC lipids in EuGr. DGTS and PC lipid classes were targeted using tandem MS by monitoring for the lipid headgroup fragment ions m/z 236 and m/z 184 indicative of DGTS and PC lipids, respectively. FIG. 15 shows extracted ion chromatograms of fragment ions indicative of PC and DGTS lipids found in EuGr and ChRe cells, respectively. Cell types were clearly separated using DGTS and PC fragment ion signals. Cell identification was confirmed using a series of microscopy images of the droplet ejection area immediately before ejection of the cell. Of the 500 cells analyzed in this preliminary experiment, comparison of DGTS and PC fragment ion peak areas were able to identify each cell type with 100% accuracy.

The single cell analysis of EuGr and ChRe cell mixture shown in FIG. 15 used a 100 µL/min flowrate with a 90/10/0.1 (v/v/v) methanol/chloroform/formic acid solvent composition. The mass spectrometer was configured to acquire SWATH mass spectra with a m/z 700-800 acquisition scan window. A m/z 100-300 scan range, 0.05 s accumulation time, IS=5500 V, DP=35 V, CE=48 eV, CES=15 eV, TEM=400° C., GS1=90 and GS2=60 nebulizer gas settings were used. Extracted ion chromatograms (XIC) of ions at m/z 184.15 (PC headgroup) and m/z 236.24 (DGTS headgroup) were used.

To show that such chemical classifications could be conducted in real-time a software solution, SCPAssistant v1.20© was used to extract single cell mass spectra while the experiment was in progress. As a proof-of-concept experiment, real-time cellular classification of the ChRe and EuGr cell mixture was conducted for the acquisition of 87 cells. Using lipid headgroup ions m/z 236 and m/z 184, automatic classification of each cell was achieved within ~3 s after acquisition. These identifications were confirmed through imaging of the sample cartridge immediately before and after droplet ejection and DGTS and PC fragment ions XICs. Identification was 100% accurate for this cell mixture. Such on-line chemical classification could conceivably be used to classify and differentiate any cellular mixture (e.g., in blood or for tumors) using a reference library of cell mass spectra.

Figure 16:
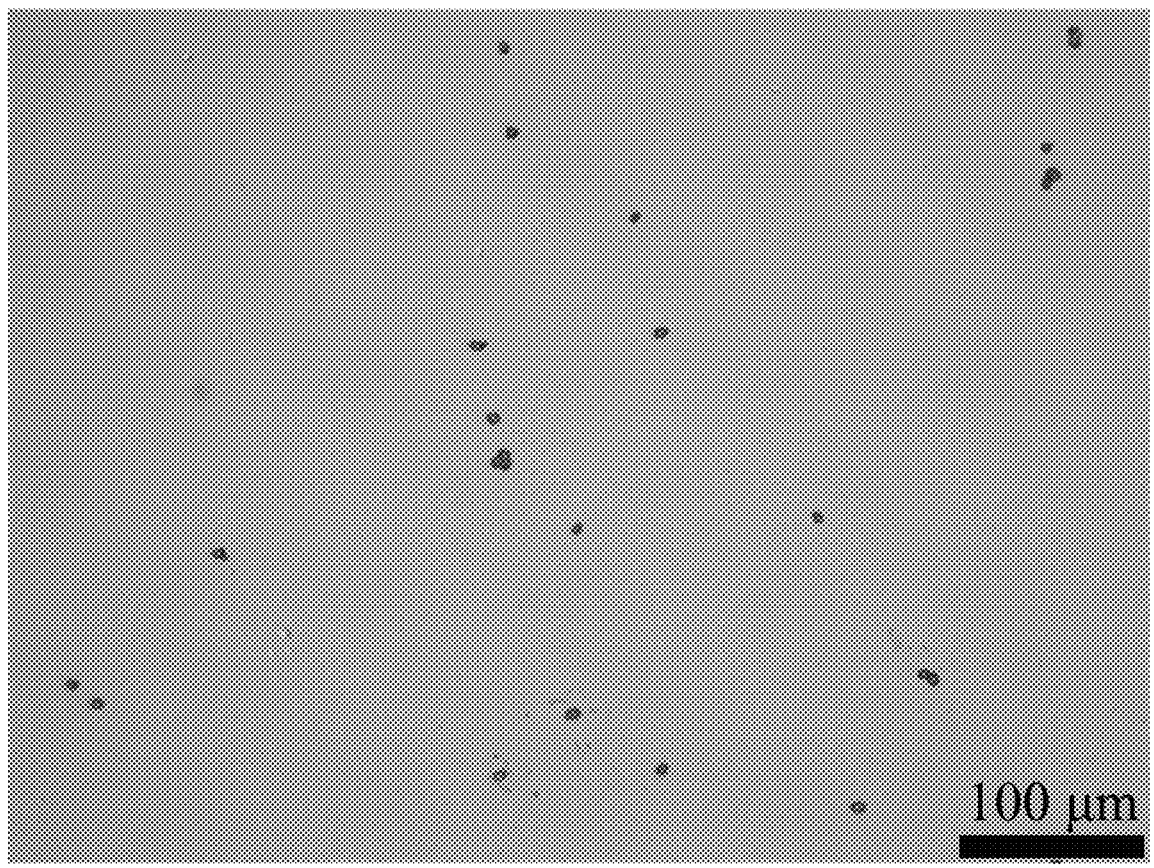
FIG. 16 is an image of a collection of intact cells on glass after spraying a cellular suspension in HSM media, without lysis.
Figure 17:
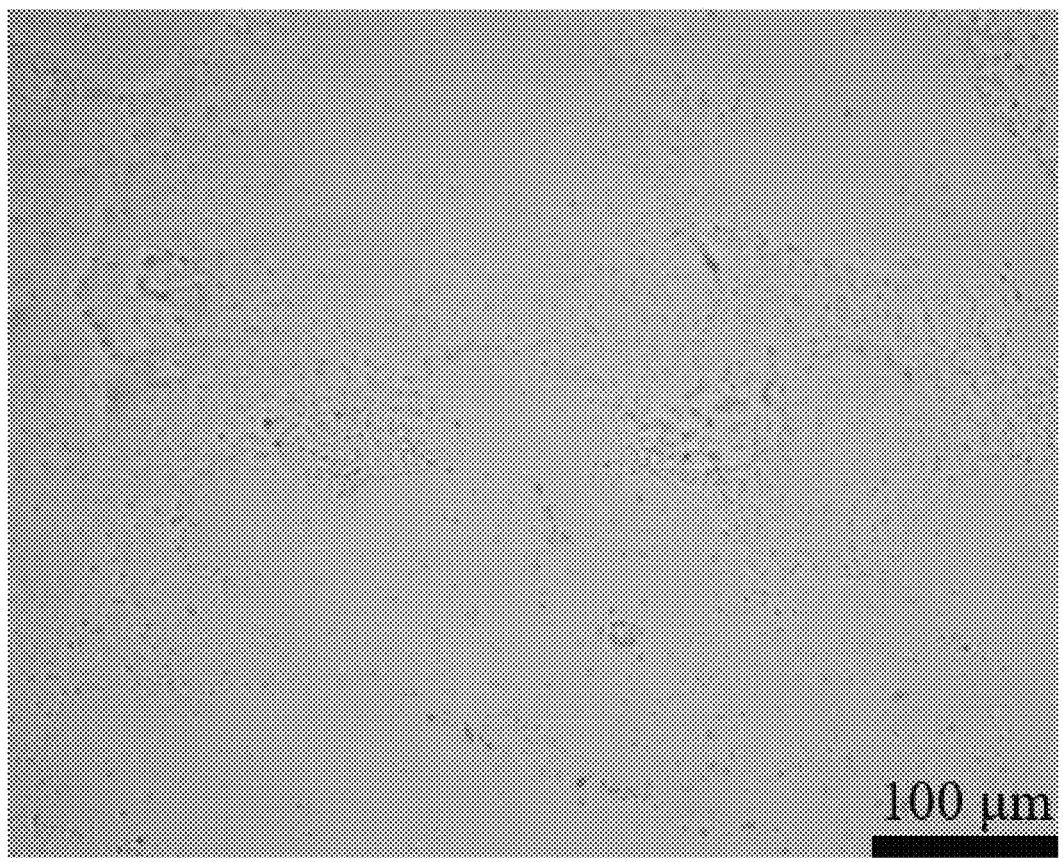
FIG. 17 is an image of a collection of nebulized droplets with lysis from exposure to liquid vortex in the capture probe.

Nutrient deprivation is a known route to perturb lipid and metabolite concentrations of ChRe. Quantitation requires the cell to be fully lysed, the molecular constituents fully extracted, and matrix suppression effects, due to cellular media or from cellular metabolites, to be normalized. Collection of LVC-electrosprayed material after single cell droplet ejection and exposure to LVC solvent indicate that cells are efficiently lysed in the system. FIG. 16 shows cell lysis after LVC capture and electrospray, and the collection of intact cells onto microscope slide after spraying cells in HSM medium directly (i.e. no solvent or voltage). FIG. 17 shows the collection of nebulized droplets after SCP-LVC with solvent (methanol). No evidence of intact cells was observed, indicating cells are lysed after exposure to LVC probe solvent and nebulization.

Figure 18:
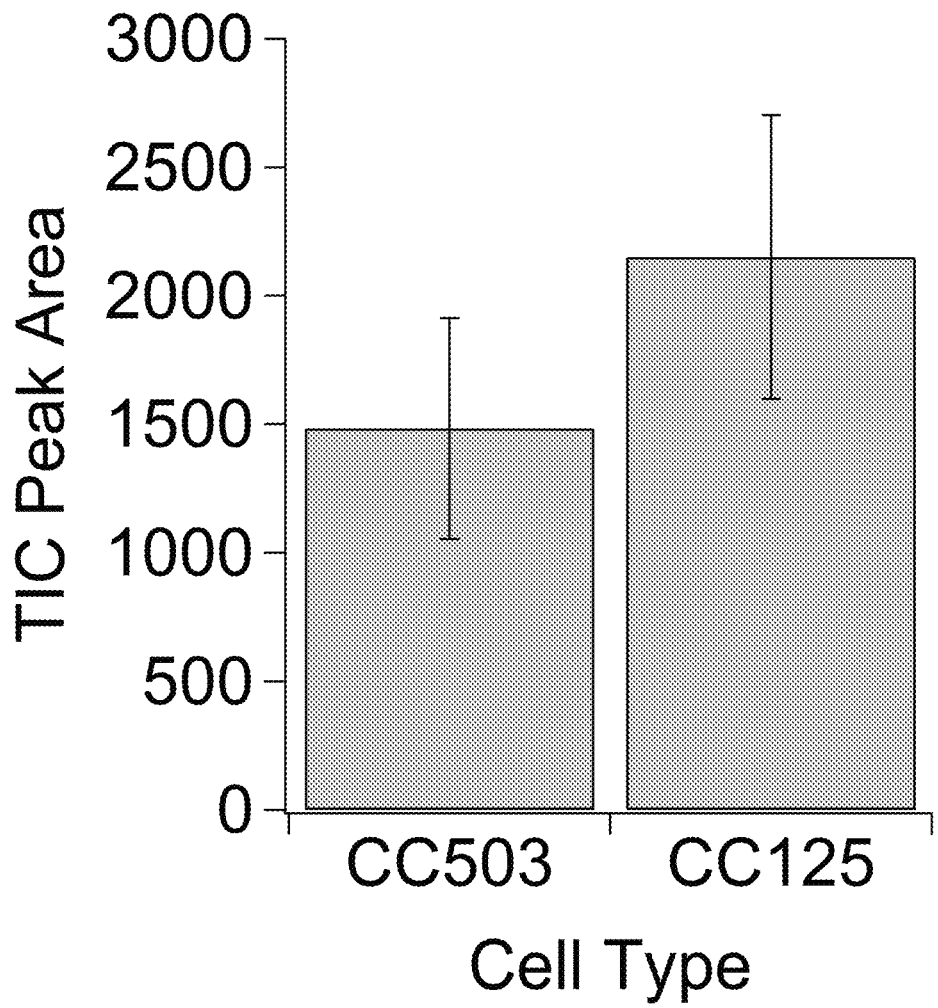
FIG. 18 is a plot of total ion chromatogram (TIC) peak area for CC503 and CC125 cell type.

FIG. 18 shows average integrated TIC peak areas between CC503 (cell wall-less) and CC125 (normal) ChRe cells. Signal levels from CC125 were not significantly lower than CC503 (wall-less mutant), indicating that CC125 cells are lysed even with the presence of a cell wall. To normalize for ion suppression effects, 1 nM of DGTS(32:0) was added to the LVC sample probe solvent and was monitored continuously. The DGTS(32:0) lipids was selected because the ion was not observed in single cell mass spectra and was the nearest standard to the DGTS lipid class that was commercially available. CC125 measured peak area is not significantly lower than CC503 measured peak area with >95% confidence, indicating that the presence of a cell wall in CC125 does not appear to negatively influence LVC-MS analysis. Physical examination of cells and the overall agreement of average cellular intensities all confirm near 100% lipid extraction of soluble analytes from single cells in these experiments.

Figure 19:
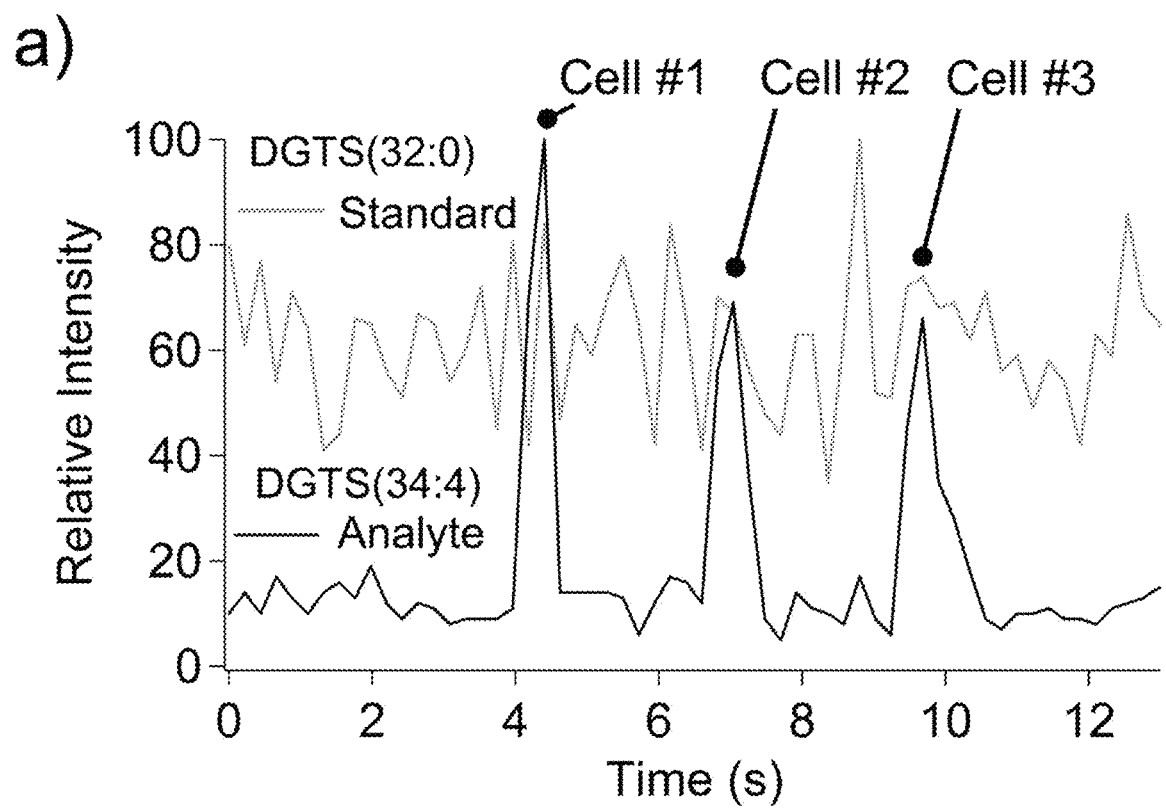
FIG. 19 is an extracted ion chromatogram (XIC) plot of relative intensity vs. time (s) for m/z 732.6 corresponding to DGTS (34:4) and m/z 712.6, corresponding to the DGTS (32:0) internal standard.

FIG. 19 shows the XIC of m/z 732.6, corresponding to DGTS(34:4) from single cells, and m/z 712.6, corresponding to the DGTS(32:0) internal standard. Average quantitative peak areas are shown for DGTS(34:4) (FIG. 20), DGTS(34:3) (FIG. 21) and DGTS(38:4) (FIG. 22) lipids derived from bulk lipid extract (light grey) and single cell (dark grey) data of cells undergoing nitrogen limited (−N) and normal (+N) growth. An asterisk "*" indicates the two means are equivalent (p<0.05). The single cell analysis of +N and −N ChRe cells shown in FIGS. 19-22 used a 150 μL/min flowrate with a 90/10/0.1 (v/v/v) methanol/chloroform/formic acid +2 μL/min 1.4 μM DGTS(32:0) solvent composition. The mass spectrometer was configured to acquire TOF mass spectra (m/z 700-1000, 0.10 s accumulation time, IS=5500 V, DP=70 V, TEM=400° C., GS1=90 and GS2=60).

Average single cell measurements were compared to bulk lipid extracts using the Bligth and Dyer extraction protocol, a common method to measure aggregate lipid composition. The modified Bligth and Dyer extraction protocol was as follows. 0.5 mL of nitrogen deprived (−N) cells, normal growth cells (+N), and HSM media (blank) were pipetted into glass vials. 3 mL 2:1 (v/v) chloroform/methanol was added to each vial. 15 μL of 21 μM DGTS(32:0) was added to each vial (internal standard). Then each vial was vortexed for 30 s. 1 mL of chloroform was then added to each vial and vortexed for 30 s. 1 mL of water was added to each vial and then was vortexed for 30 s. Each vial was centrifuged for 5 min at 2260 RPM (Eppendorf 5430 centrifuge, Hamburg, Germany). The lipid extract was pipetted out into an additional glass vial. Two additional extracts were performed by adding 1 mL of chloroform, vortexing for 30 s, centrifugation and removal of lipid extract. The collected lipid extract was dried using $N_2$ gas and then re-suspended in 0.5 mL 90/10/0.1 (v/v/v) methanol/chloroform/formic acid. 2 μL/min of extract mixed with 150 μL/min 90/10/0.1 (v/v/v) methanol/chloroform/formic acid were measured by ESI-MS. The mass spectrometer was configured to acquire TOF mass spectra (m/z 700-1000, 0.10 s accumulation time, IS=5500 V, DP=70 V, TEM=400° C., GS1=90 and GS2=60).

The dilution of the cell in the LVC probe solvent can be calculated using the LVC flowrate, generally 150 μL/min, and the single cell signal peak width, ~1.2 s, which indicates that each cell was contained within 3 of solvent. Given the Gaussian-like peak shape of the signal profile, majority of analyte (~1 sigma/68%) lies within 0.4 s or ~1 μL of solvent.

Figure 20:
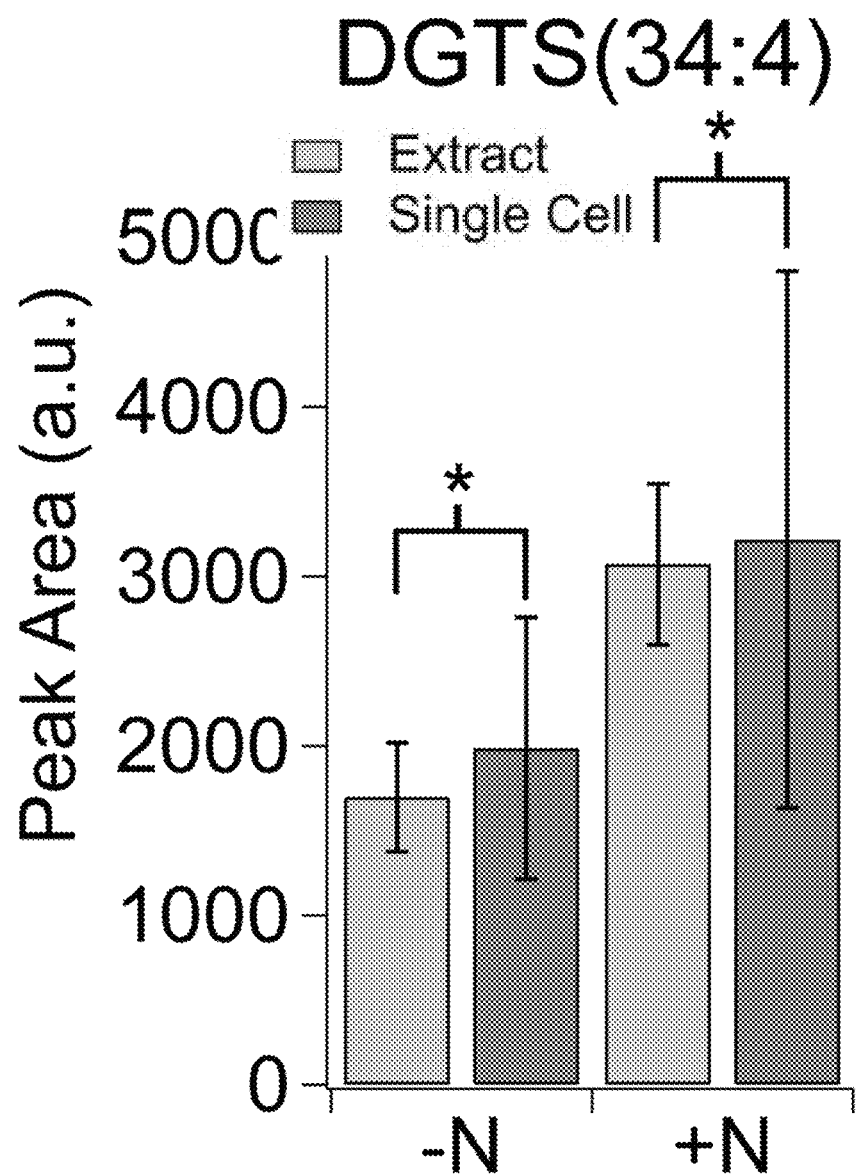
FIG. 20 is a plot of peak area (a.u.) for nitrogen limited (−N) and normal (+N) growth, for DGTS (34:4), measured from single cells and from extracts.
Figure 21:
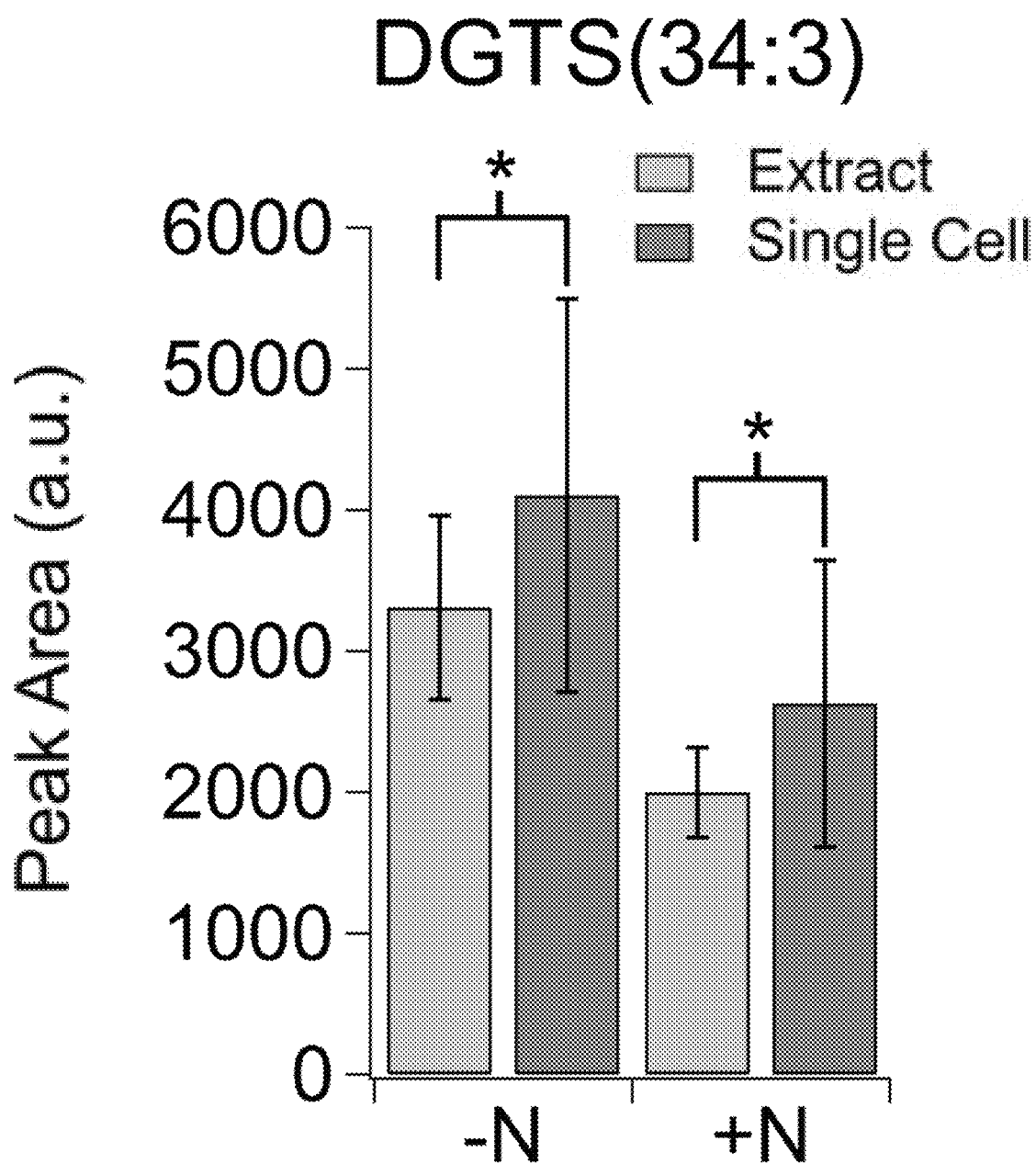
FIG. 21 is a plot of peak area (a.u.) for nitrogen limited (−N) and normal (+N) growth, for DGTS (34:3), measured from with single cell and extract.
Figure 22:
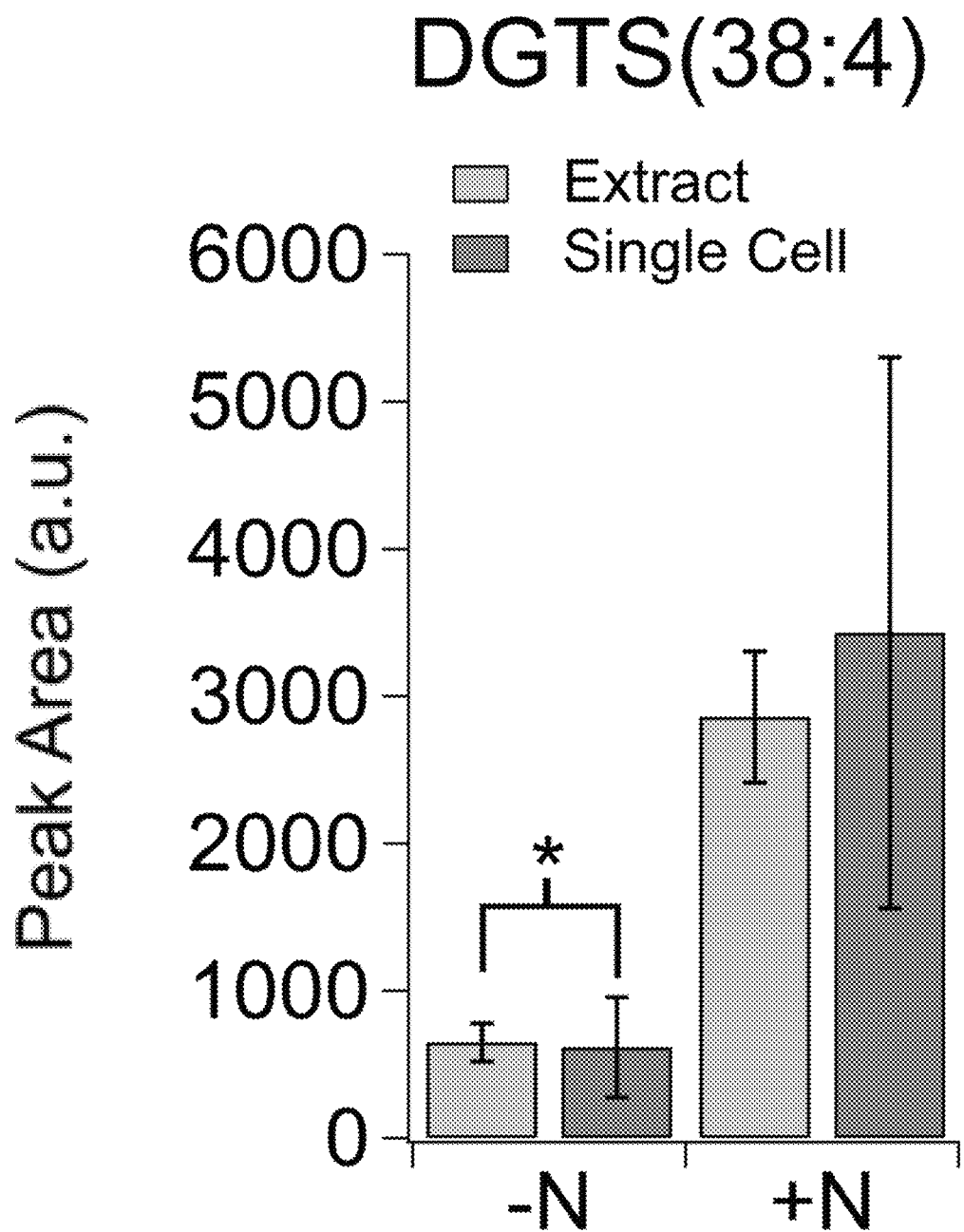
FIG. 22 is a plot of peak area (a.u.) for nitrogen limited (−N) and normal (+N) growth, for DGTS (38:4), measured from with single cell and extract.

Quantified peak area/cell of DGTS(34:4), DGTS(34:3), and DGTS(38:4) lipids after 5 days of growth were calculated from the acquisition of 556 and 704 single cells for +N and −N growth conditions, respectively (FIGS. 20-22). Lipid extract and average single cell data could be considered equivalent for all but the +N, DGTS(38:4) experiment. For equivalence testing a standard error at 95% confidence of the extract measurement was used to define the confidence level limits for single cell measurements to be considered equivalent. Absolute quantitation could be achieved by using an external calibration curve of each molecule in question, but in the present case standards of these specific lipids were not available.

There were notable mass spectral differences between +N and −N growth. Cell suspensions were notably different in color with +N growth being significantly greener. This is consistent with greater pheophytin a, chlorophyll a and chlorophyll b peak areas observed in +N cells. Cell growth differed greatly between nutrient conditions, with −N growth cell number concentrations remaining relatively stagnant over the 5 days of the experiment. Cell size distributions, measured using the image recognition algorithm of the Single-Cell Printer, were similar between both growth conditions. The cell size distribution data is influenced by the image recognition algorithm settings, which in this case were set to allow acquisition of cells with diameters between 5-25 μm. Single cell peak area histograms from DGTS(34:4), DGTS(34:3), DGTS(38:4), MGDG(34:7), pheophytin a, and chlorophyll a ions observed in ChRe for +N and −N experiments and these ions peak areas were significantly greater for normal growth conditions. DGTS (34:4) and DGTS(34:3) lipids had very different distributions despite the similarity between molecules. This was also apparent in cell extract data.

These data demonstrate that the invention enables untargeted, high throughput and quantitative mass spectrometric analysis of single cells in their native media. The invention demonstrates the untargeted and targeted acquisition of single cell mass spectra of microalgae and HeLa cells with high throughput (~2.5 s/cell). Real-time chemical classification of single cells can be achieved, using software, based on chemical differences observed in mass spectra. The ability to acquire SWATH spectra in addition to TOF-MS spectra can help to chemically differentiate more complex cell systems. The system was used to quantitate lipids and show their distribution in single cells grown under +N and −N conditions through the incorporation of an internal standard to the solvent flow of the LVC system.

The experiments shown measured single cell chemistry directly from the cell culture without very little, if any, sample preparation procedures which could negatively perturb cells. The lack of time-consuming and costly sample pre-treatment protocols significantly improves the ease and overall speed of single cell experiments and enables the potential of in situ chemical profiling of raw samples (e.g., water samples). Nearly any cell suspension is amenable to analysis by the invention, including mammalian cells. Targeted mammalian cell analysis identifications are also possible. Currently, media should have viscosities similar to water to be reliably ejected. Also, there is a small chance (<5%) that multiple cells could be contained in the same droplet, but those are rare events and most of them can be identified by additional post-analysis of the images generated by the SCP. Ejection of smaller cells than those used herein (e.g., bacteria) is possible but will depend on LVC-MS sensitivity to molecules of interest. The invention has the potential to elucidate fundamental cellular processes that are otherwise obfuscated by removing cells from their native environment. Short sample-to-answer time, and the combination of single-use dispensing cartridges with a self-cleaning LVC probe makes the invention potentially viable for future clinical applications, and may provide insights into how non-genetic heterogeneity of cellular metabolites and lipids influence the efficacy of therapeutics, leading possibly to improved therapeutic strategies.

The invention allows for a number of unique experiments to be performed. The removal of extensive sample preparation procedures which can negatively perturb cells make this single cell characterization capability much more accessible. From a single cell several mass spectra can be acquired in both an untargeted and targeted manner. All experiments shown herein measured single cell chemistry directly from the cell culture. Video images of the cell before and after droplet ejection are used to calculate cell diameter and to validate that single cells are predominantly ejected and acquired by the system. The ability of the system to quantitate lipid peak areas at the single cell level through the incorporation of an internal standard to the solvent flow of the system was demonstrated. Quantitative values were validated by comparing the average of single cell measurements to that measured from bulk lipid extracts. While the targeted lipid had a <15% difference in values between bulk lipid extracts, other lipids could be quantitated as well including lipids outside of the internal standard class, though this needs to be evaluated on a case by case basis.

In comparison to flow cytometry and mass cytometry instrumentation, the invention offers untargeted chemical profiling of cellular metabolites from unperturbed and un-modified cells. While flow cytometry is generally limited to one or a few molecular tags and mass cytometry to several dozen, the invention could incorporate potentially hundreds of molecular tags. Further, it is not limited to the use of fluorophores or to metal isotopes, though either could also be used sensitivity permitting. While throughput is significantly slower as compared to conventional flow cytometry techniques, the data presented here represents a substantive increase over the current state of the art. The lack of time-consuming and costly sample pre-treatment protocols significantly reduces the throughput of each experiment and improves the accessibility. Single cell data could be acquired up to a theoretical rate of 1 cell/s, in practice this was ~1 cell/2.5 s.

Nearly any cell suspension is amenable to analysis by this technique, including mammalian cells. While the focus has been to establish the proof of concept of the SCP-LVC-MS system, targeted mammalian cell studies are feasible potentially from human samples. One limitation of the technology is the droplet ejection mechanism. Currently, media must have viscosities similar to water to be reliably ejected. Also, there is a small chance that multiple cells could be contained in the same droplet due to dark edges along the sample cartridge. The smallest cell size is dependent on the orifice of the sample cartridge, ability to visualize the single cell in the sample cartridge and the mass spectrometer sensitivity to the molecules of interest.

The invention as shown in the drawings and described in detail herein discloses arrangements of elements of particular construction and configuration for illustrating preferred embodiments of structure and method of operation of the present invention. It is to be understood however, that elements of different construction and configuration and other arrangements thereof, and methods of operation other than those illustrated and described may be employed in accordance with the spirit of the invention, and such changes, alterations and modifications as would occur to those skilled in the art are considered to be within the scope of this invention as broadly defined in the appended claims. In addition, it is to be understood that the phraseology and terminology employed herein are for the purpose of description and should not be regarded as limiting.

I claim:

1. A method for analyzing single cells by mass spectrometry from a sample containing a plurality of cells, comprising the steps of:
   providing a plurality of cells and a liquid medium;
   placing the cells and liquid medium in a single cell isolation and ejection system;
   releasing liquid medium containing a single cell from the single cell isolation and ejection system;
   capturing the liquid medium and single cell in a capture probe containing a flowing capture probe solvent, the capture probe comprising a coaxial probe wherein the capture probe solvent flows from a coaxial supply flow path, overflows a common open end of the coaxial probe and enters a coaxial solvent exhaust flow path;
   lysing the cell with a lysis inducer in the capture probe to disperse single cell components into the liquid medium, wherein the capture probe solvent provides a lower partial pressure than the internal pressure of the cell to cause lysis of the cell;
   transporting the lysed single cell components to a mass spectrometer through the coaxial solvent exhaust flow path, where the lysed single cell components entering the mass spectrometer are spatially and temporally separated from any dispersed components of another single cell from the sample entering the mass spectrometer; and,
   conducting mass spectrometry on the lysed single cell components.

2. The method of claim 1, wherein the capture probe solvent comprises at least one selected from the group consisting of methanol, ethanol, isopropranol, hexane, chloroform, dichloromethane, acetonitrile, and water.

3. The method of claim 1, wherein the lysis is additionally induced by a chemical lysing agent.

4. The method of claim 3, wherein the chemical lysing agent comprises at least one selected from the group consisting of sodium dodecyl sulfate (SDS), Triton-X, NP-40 lysis buffer, RIPA lysis buffer, Tween lysis buffer, CHAPS lysis buffer, and perfluorooctanoic acid.

5. The method of claim 1, wherein the lysis is additionally induced by a liquid vortex formed by the flowing capture probe solvent in the coaxial solvent exhaust flow path.

6. The method of claim 5, wherein the liquid vortex fluid rate is 50-300 µL/min and has a 0.5-20 second elution time.

7. The method of claim 1, wherein the lysis is additionally induced by the application of 0.2-1.5 volts across the cell for 1-10000 µs to the cell in the capture probe solvent.

8. The method of claim 1, wherein the lysis is additionally induced by an acoustic wave emitted at the cell in the capture probe having a frequency of 15-20 kHz for 0.1-10 seconds.

9. The method of claim 1, wherein the release rate of the single cell isolation and ejection system is from 0.1 cell/s to 100 cells/s.

10. The method of claim 1, wherein the liquid medium comprises a cell culture medium.

11. The method of claim 1, wherein the release rate of the single cell isolation and ejection system is drop on demand.

* * * * *